United States Patent
Durrat et al.

(10) Patent No.: US 8,076,466 B2
(45) Date of Patent: Dec. 13, 2011

(54) SACCHARIDIC FLUORESCENT SUBSTRATES, THEIR PROCESS OF PREPARATION AND THEIR USE

(75) Inventors: François Durrat, Grenoble (FR); Isabelle Texier-Nogues, Grenoble (FR); Véronique Robert, Grenoble (FR)

(73) Assignee: Commissariat a l'Energie Atomique, Paris (FR)

( * ) Notice: Subject to any disclaimer, the term of this patent is extended or adjusted under 35 U.S.C. 154(b) by 547 days.

(21) Appl. No.: 12/206,254

(22) Filed: Sep. 8, 2008

(65) Prior Publication Data

US 2009/0081634 A1 Mar. 26, 2009

(30) Foreign Application Priority Data

Sep. 10, 2007 (FR) .................................... 07 06313

(51) Int. Cl.
*C07H 15/203* (2006.01)
*A61K 31/7032* (2006.01)
*A61K 31/7034* (2006.01)

(52) U.S. Cl. ........ 536/17.8; 514/25; 536/17.9; 536/18.2

(58) Field of Classification Search ........................ None
See application file for complete search history.

(56) References Cited

U.S. PATENT DOCUMENTS

| 5,621,002 | A | * | 4/1997 | Bosslet et al. | ................ 514/451 |
|---|---|---|---|---|---|
| 7,754,694 | B2 | * | 7/2010 | Ahmed et al. | ................... 514/25 |
| 2006/0147378 | A1 | * | 7/2006 | Tung et al. | ..................... 424/9.6 |
| 2007/0009980 | A1 | | 1/2007 | Graham | |
| 2008/0241128 | A1 | * | 10/2008 | Jeffrey | ....................... 424/130.1 |

OTHER PUBLICATIONS

Bouvier et al., "A new paclitaxel prodrug for use in ADEPT strategy" Org. Biomol. Chem. (2003) vol. 1 pp. 3343-3352.*
Nan-Hui Ho, et al., "A Self-Immolative Reporter for β-Galactosidase Sensing", ChemBioChem, XP-002477908, vol. 8, 2007, pp. 560-566.

* cited by examiner

*Primary Examiner* — Eric S Olson
(74) *Attorney, Agent, or Firm* — Oblon, Spivak, McClelland, Maier & Neustadt, L.L.P.

(57) ABSTRACT

The present invention relates to fluorescent enzymatic substrates of saccharidic nature having a self-cleavable spacer arm functionalized by a fluorophore F and by at least one inhibitor of the fluorescence of F, to the use thereof for preparation of a diagnostic reagent for functional imaging in vivo, and to the diagnostic reagent for functional imaging containing at least one such enzymatic substrate.

27 Claims, 2 Drawing Sheets

F* = Fluorescent fluorophore

US 8,076,466 B2

SACCHARIDIC FLUORESCENT SUBSTRATES, THEIR PROCESS OF PREPARATION AND THEIR USE

CROSS REFERENCE TO RELATED APPLICATIONS

This application claims priority to French Application No. 0706313, filed Sep. 10, 2007, the disclosure of which is incorporated herein by reference in its entirety.

BACKGROUND OF THE INVENTION

The present invention relates to fluorescent enzymatic substrates of saccharidic nature having a self-cleavable spacer arm functionalized by a fluorophore F and by at least one inhibitor of the fluorescence of F, to the use thereof for preparation of a diagnostic reagent for functional imaging in vivo, and to the diagnostic reagent for functional imaging containing at least one such enzymatic substrate.

Fluorescence is a very widely used technique for detection of enzymatic activities in vitro. It is an inexpensive, fast and generally highly sensitive technique. Numerous enzymes of significant biological importance have substrates in the form of saccharidic derivatives, which can be used in particular to perform enzymatic assays on biological samples (blood, urine, etc.), on cells (fixed or in culture) or even on tissues (tissues of euthanized animals, biopsies).

Applications that seem equally promising are the in vivo applications, especially for fluorescence imaging of small animals. In fact, reporter genes expressing different enzymes such as β-galactosidase (β-gal), β-glucuronidase (β-glu), chloramphenicol, acetyltransferase, luciferase, fluorescent proteins such as "Green Fluorescent Protein" (GFP) are now very widely used in biology to study gene expression (transcription and translation of DNA in proteins), transfection or other biological processes. The reporter genes can act as indicators to demonstrate the introduction and transcription of another gene of interest situated on the same coding part of the DNA. The DNA constructs containing the reporter genes are introduced into the animal to form transgenic animals. For example, the number of transgenic mice already constructed is very large and growing rapidly. In a very large number of cases, the marker gene used is the lacZ gene, which codes for β-gal of E. coli. Another example of an equally used marker gene is the gusA gene, which codes for β-glu of E. coli. As it happens, the substrates of the enzymes expressed by certain of these genes, and in particular by the lacZ and gusA genes, are saccharidic derivatives. It is therefore very important to have saccharidic substrates available in order that the activity of such enzymes can be detected.

Numerous substrates of saccharidic nature already exist for detection of enzymatic activities, such as, for example, the enzymatic activities of β-gal and β-glu. These enzymatic substrates can be, in particular:
 substrates for nuclear imaging,
 chemiluminescent substrates such as the substrates sold under the trade names Lumi-Gal® 530 by Lumigen Inc. (USA) and Galacton-Star® by Applied Biosystems (USA);
 substrates for dielectrophoretic detection,
 substrates for MRI,
 substrates forming precipitates,
 substrates for spectrophotometric assays, including the X-gal substrate (5-bromo-4-chloro-3-indolyl-beta-D-galactopyranoside), sold, for example, under the trade name BlueTech® by Mirador DNA Design Inc.; and
 fluorescent substrates.

Ideally, these substrates should have the following properties:
 fast enzymatic reaction kinetics,
 low Michaelis constant,
 large difference between the properties of interest of the substrate and those of its product(s) (properties of interest: absorption for a chromogenic substrate, fluorescence for a fluorogenic substrate, etc.).

The interest in fluorescent substrates compared with the other substrates described hereinabove is their detection sensitivity and the low cost of the instrumentation necessary to use them. In common with MRI, they make it possible under certain conditions to achieve enzymatic detection in vivo.

In general, the fluorescent enzymatic substrates function according to the following principle: a substrate that does not fluoresce in the detection wavelength region produces a product that fluoresces in that same wavelength region when it is brought into the presence of an enzyme whose activity is to be detected and which is specific to the substrate used. It is therefore necessary to find fluorophores whose fluorescence is initially inhibited when they are grafted onto the substrate and can be liberated after reaction with the enzyme whose activity is to be detected. The choice of commercially available fluorophores is therefore limited by this constraint of initial inhibition of the fluorescence when the fluorophore is fixed on the enzymatic substrate.

In vivo, the recent development of optical methods is opening new horizons for functional imaging. It is now possible to follow, in real time and in non-invasive manner, gene expression in animals, especially in the mouse, after anesthesia. Optical imaging offers a certain number of advantages compared with the other functional imaging techniques, such as magnetic resonance imaging (MRI), positron emission tomography (PET) and single photon emission computed tomography (SPECT):
 it obviates the handling of radioactive molecules, therefore removing the attendant constraints and risks (radioprotection, waste management, synchrotron source for the PET markers);
 it does not necessitate large investments in instrumentation;
 it has good sensitivity compared with MRI, in terms of the amount of marker injected.

Optical imaging makes use of fluorescent enzymatic substrates.

When the presence of enzymatic activity is to be detected in vivo, for example in a small laboratory animal such as the mouse, very few fluorescent molecules are available for this application. In fact, to ensure that the exciting light and the light emitted by the fluorophore can pass through the tissues, it is advisable to use fluorophores that absorb and emit in the near infrared, or in other words at a wavelength between 640 and 900 nm. As it happens, very few molecules that fluoresce in this wavelength region are commercially available at present (largely limited to the cyanines). The double constraint, or in other words the initial inhibition of fluorescence when the fluorophore is fixed on the substrate and the use of a fluorophore that absorbs and emits in the near infrared, is undoubtedly the reason for the lack of fluorescent enzymatic substrates of saccharidic nature in this wavelength region.

In fact, most fluorescent enzymatic substrates of saccharidic nature currently available on the market are not constructed on the basis of fluorophore groups that absorb and emit in the near infrared. For example, it is possible to procure:
 substrates based on fluorescein, for detection of β-gal activity, among which there may be mentioned, for example, FDG (fluorescein-di-β-D-galactopyranoside) (excitation 490 nm/emission 514 nm) or one of its derivatives;

substrates based on coumarins or umbelliferones, for detection of β-gal, β-glu or phosphatase activities, such as the substrates MUG (4-methylumbelliferone β-D-galactopyranoside), DiFMUG (6,8-difluoro-4-methylumbelliferyl β-D-galactopyranoside), MUP (4-methylumbelliferone phosphate), DiFMUP (6,8-difluoro-4-methylumbelliferyl phosphate) and derivatives (excitation 350-380 nm/emission 450-470 nm); or else substrates based on resorufin and derivatives, especially for detection of lipase (excitation 570 nm/emission 585).

Most fluorescent substrates that are commercially available at present function according to the principle represented in Scheme A below:

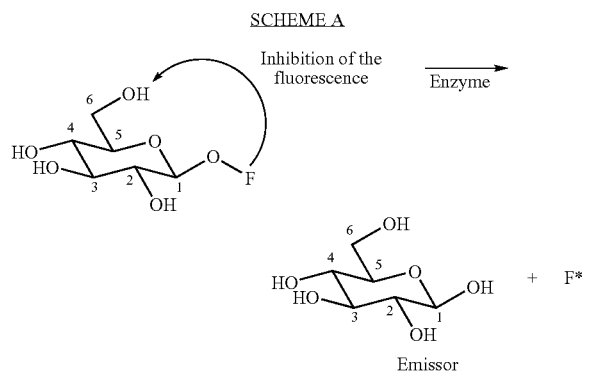

In this scheme, the fluorophore F is grafted at anomeric position 1 (anomeric bond of β configuration) onto a monosaccharide, β-glucopyranose, to form the enzymatic substrate. This substrate must be weakly fluorescent before the reaction with the enzyme. The fluorophore groups must therefore be chosen in such a way that their fluorescence can be initially inhibited by the monosaccharide. The enzymatic reaction induces cleavage of the anomeric bond and liberates the fluorophore group. When the fluorophore group is distant from the monosaccharide, its fluorescence is no longer inhibited and it can then emit a signal that is detected by means of a spectrofluorimeter. The emitted signal corresponds to the enzymatic activity and, within a certain concentration range, is proportional to the enzyme concentration.

Nevertheless, the substrates functioning according to the principle illustrated in Scheme A exhibit a certain number of disadvantages:

the choice of fluorophore group is limited by the fact that its fluorescence must be capable of being inhibited when it is grafted onto the sugar; not all fluorophore groups have this property, especially in the near infrared region when the capability of detection in vivo is desired (see the foregoing). Thus the commercial fluorogenic substrates always have fluorophores of the same families: coumarins, umbelliferones, fluoresceins, resorufins. In the near infrared region in particular, this limitation is even more constraining, because the number of molecules that exist in this wavelength region is already small.

if inhibition of the fluorescence by the sugar is not complete, the detection sensitivity of the system is poor. To remedy this problem, certain manufacturers propose substrates in which the fluorophore group is bound to 2 saccharidic units by anomeric position 1. An example of this type of substrate is FDG. The initial inhibition of fluorescence is effectively increased by doubling the number of saccharidic units bonded to the fluorophore group. Nevertheless, the liberation of the fluorophore group and therefore of the fluorescence then also necessitates two enzymatic cleavages instead of one, and the detection sensitivity is therefore improved only slightly in such a system.

The only commercially available enzymatic substrate that absorbs and emits in the near infrared is the substrate DDAOG, which is a conjugate of β-galactoside (G) and of 7-hydroxy-9H-(1,3-dichloro-9,9-dimethylacridin-2-one) (DDAO), used for detection of β-gal activity and sold by the Molecular Probes Co. (USA). This substrate absorbs at 645 nm and emits at 660 nm. Its mode of functioning, as described by Tung C.-H. et al., Cancer Research, 2004, 64, 1579-1583, is represented in Scheme B below:

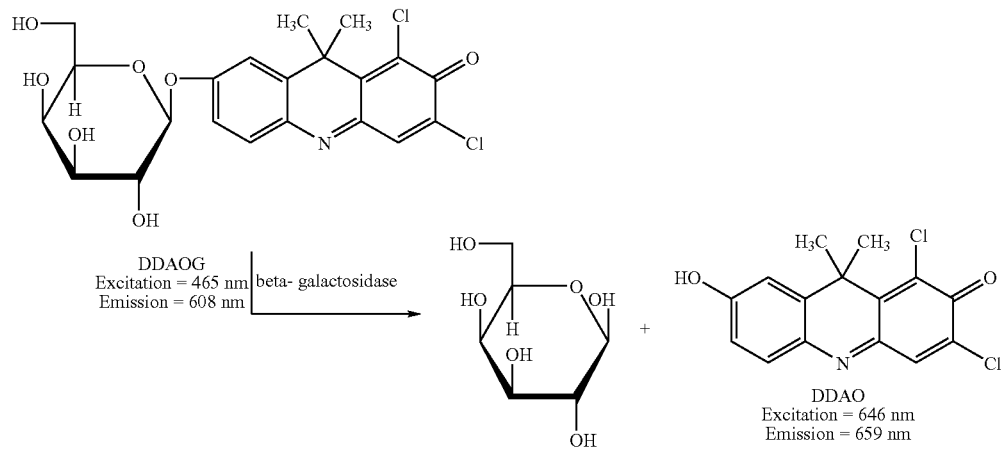

However, even though this particular substrate absorbs and emits in the near infrared, it also exhibits a certain number of disadvantages:

its fluorescence is not completely inhibited when the fluorophore group is bonded to the saccharidic unit, which produces an initially non-negligible background noise and lowers the detection sensitivity. Thus, in the in vivo experiment described in the aforesaid article of Tung C.-H. et al., it can be seen that the injected DDAOG dose (0.5 mg) and the necessary exposure time (2 minutes) are very large compared with the traditional amounts and exposure times for applications of this type (generally 10-50 μg of substrate injected for an exposure time of 20 to 100 ms);

the absorption and emission spectra of the DDAO are very narrow and very close to one another, thus necessitating very good optical filtering to detect the signal relative to the initial background noise;

the absorption and emission spectra of the DDAO are still not shifted far enough into the red to be in an optimal optical window for performing in vivo imaging.

There have also been proposed, especially in French Patent Application 2888938, fluorescent substrates having a saccharidic skeleton that carries, on the same saccharidic unit, a fluorophore group on the one hand and a group that inhibits the fluorescence of the fluorophore group on the other hand, its being understood that one of these two groups occupies the anomeric position of the saccharidic unit on which both groups are fixed, the other group occupying any other position whatsoever of the saccharidic unit.

Such fluorescent substrates permit the fixation of a greater variety of fluorophore groups that absorb and emit in the near infrared and therefore can be used in vivo. However, they also are not completely satisfactory, in particular because the affinity of enzymes for such substrates is greatly reduced and makes the process too inefficient.

Finally, there has very recently been developed a saccharidic sensor known as Gal-2SBPO, which results from conjugation of the substrate of β-galactosidase (β-D-galactopyranoside: Gal) and of a fluorescent water-soluble dye, the perchlorate of 9-di-3-disulfonyl propylaminobenzo[a]phenoxazonium (2SBPO) via a spacer arm that includes a peptide. In this enzymatic substrate (Gal-2SBPO), the fluorescence is inhibited by the peptide (glycine) included in the spacer arm connecting the saccharidic unit Gal and the fluorophore group 2SBPO proper (HO, N.-H. et al., Chem. Bio. Chem., 2007, 8, 560-566). The enzymatic activity of β-galactosidase induces cleavage between the sugar and the spacer arm, and the fluorophore group can then fluoresce after a final hydrolysis that separates it from its inhibitor peptide. The mode of functioning of this enzymatic sensor can be represented by the following Scheme C:

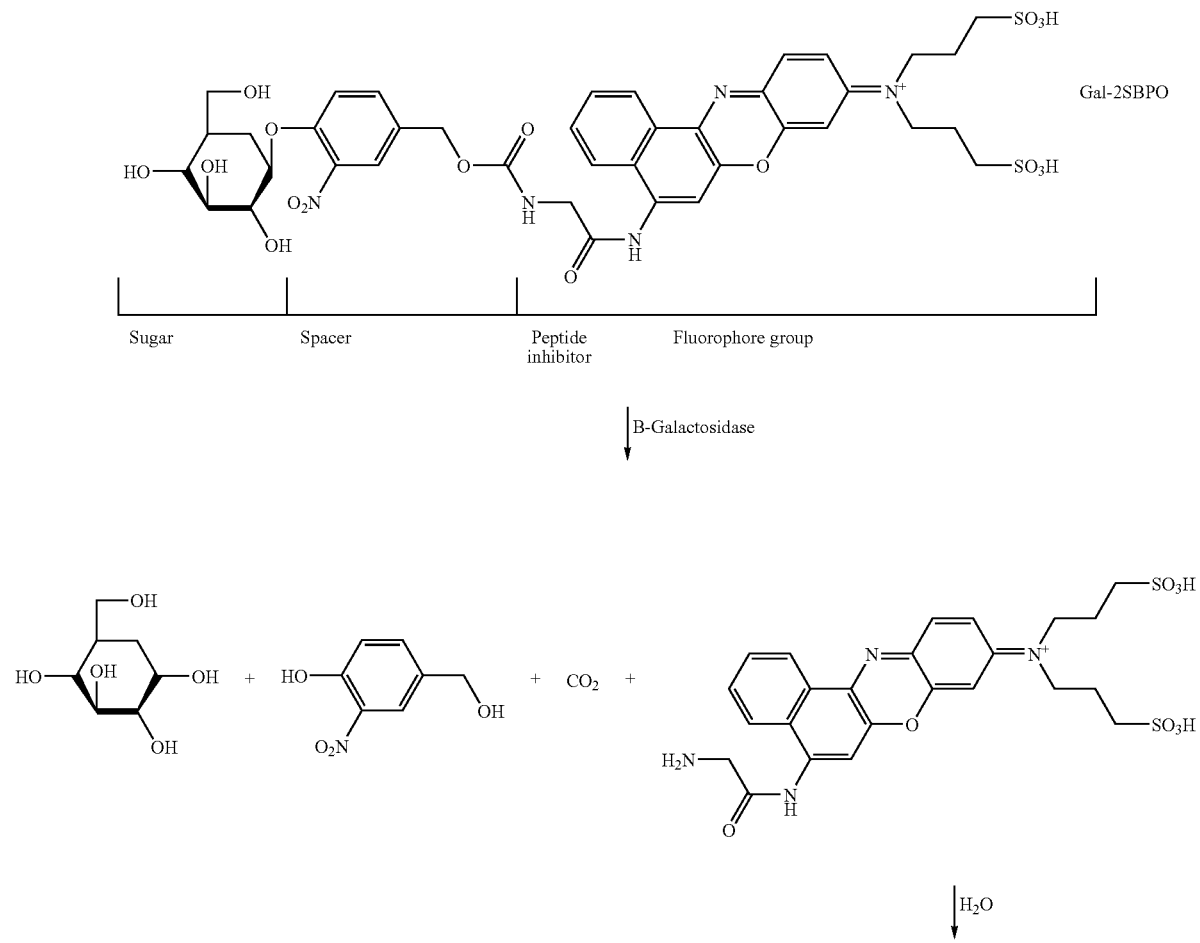

Glycine + 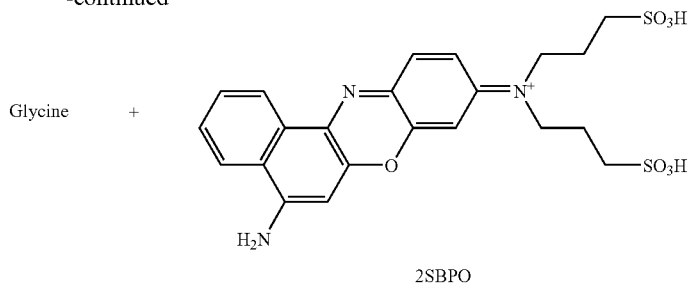

2SBPO

However, such a system still exhibits a certain number of limitations:
- the choice of fluorophore is restricted solely to 9-di-3-disulfonyl propylaminobenzo[a]phenoxazonium perchlorate, which at present seems to be the only fluorophore group whose fluorescence can be inhibited by the presence of an amino acid such as glycine (HO, N.-H. et al., Tetrahedron, 2006, 62, 578-585).
- the fluorescence intensity after the enzymatic activity is increased by a factor of only 7, which, given the current state of the capabilities of measuring instruments, still represents a small ratio for envisioning the use of this fluorescent marker for in vivo imaging.

It is therefore to remedy all of these problems that the inventors have developed that which is the object of the invention.

The inventors effectively made it their objective to provide a fluorescent enzymatic substrate of saccharidic nature that does not have the disadvantage of prior art substrates and that in particular is very suitable, when so desired, for use in detection of enzymatic activities in vivo.

DETAILED DESCRIPTION OF THE PREFERRED EMBODIMENTS

Figure 1:
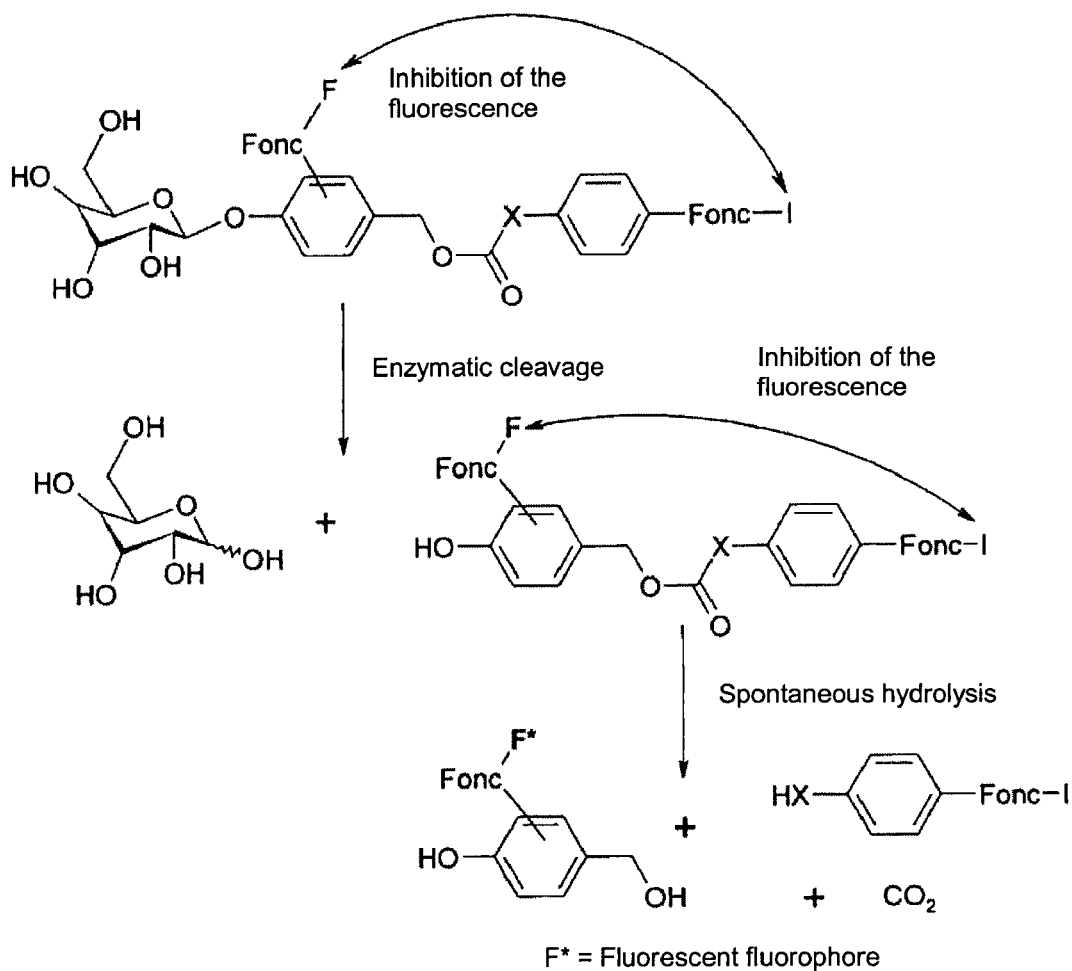
FIG. 1 shows the functionality and mode of operation of one embodiment of the present invention.

The object of the present invention is therefore a fluorescent enzymatic substrate, characterized in that it corresponds to the following structure (I):

[Sac]-B(I)F     (I)

in which:
- [Sac] is a skeleton of saccharidic nature composed of at least one saccharidic unit and chosen from among the monosaccharides, the oligosaccharides having 2 to 9 saccharidic units and the polysaccharides having at least 10 saccharidic units;
- B represents a self-cleavable spacer arm composed of one or more subunits, the said arm being fixed in anomeric position 1 of the said saccharidic unit, there being no difference in the anomeric bond in α or β position;
- F is a fluorophore group carried by the spacer arm;
- I is a group that inhibits the fluorescence of F; the said group I being a side substituent of at least one subunit of the spacer arm;
- n is an integral number equal to 1 or 2; and its being understood that the fluorophore group is not connected directly to the inhibitor group by any covalent bond.

In these enzymatic substrates of formula (I) hereinabove, the self-cleavable spacer arm connecting the saccharidic skeleton to the fluorophore group F exhibits the particular feature of dislocating spontaneously into one or more distinct subunits after the enzymatic activity, or in other words after the enzyme has caused cleavage of the bond connecting the said spacer arm to the saccharidic skeleton. This dislocation causes rupture of the bond connecting the spacer arm to the fluorophore group on the one hand and of the bond connecting the spacer arm to the fluorescence inhibitor group on the other hand, thus liberating the fluorescence of the group F.

The enzymatic substrates that correspond to the invention and are such as described hereinabove exhibit very good initial inhibition of the fluorescence, taking into account the presence of one or two groups I as side substituents of the spacer arm. In contrast to known prior art substrates, this particular configuration makes it possible:
- to broaden the choice of usable fluorophore groups: the choice of such a group is no longer limited to groups whose fluorescence must initially be inhibited by the skeleton [Sac] or by a peptide that is an integral part of a spacer arm. The choice of available fluorophore groups is therefore much broader and in particular can be extended to fluorophore groups that emit in the near infrared;
- to further increase the sensitivity of detection of the enzymatic activity: in fact, the fluorescence of the fluorophore group is inhibited by an object that has specifically this role and that is therefore much more effective than when the inhibition must be achieved by the saccharidic skeleton or by a peptide;
- to permit better affinity for the target enzyme: in fact, the act of grafting the fluorophore and the fluorescence inhibitor onto the cleavable aglycone moiety permits better affinity for the enzyme, since all the recognition sites are free,
- to increase the solubility of the substrate by virtue of the use of fluorophore groups that are much more soluble than the fluorophore groups that are commercially available at present and are generally hydrophobic,
- to facilitate the conditions of use of the enzymatic substrate by virtue of the use of fluorophores that, for example, are insensitive to the pH or to the redox potential and thus can be used more easily in vivo. In fact, certain currently used fluorophores, such as fluorescein, have emission properties that are very dependent on the pH and are poorly compatible with in vivo use, where the intracellular conditions cannot be modified. By using other fluorophores whose emission properties depend only slightly on the pH, on the redox potential or on the concentration of ions, the signal acquisition conditions and the sensitivity in vivo are facilitated.

The saccharadic units of the skeleton [Sac] of the substrates of structure (I) according to the invention can be chosen in particular from among galactose, mannose, idose, talose, rhamnose, glucose, ribose, fucose and their amino or acid derivatives, among which there can be cited in particular galactosamine, glucosamine, lactosamine, glucuronic acid, iduronic acid and sialic acid. They are preferably chosen from among glucosamine, galactose and glucuronic acid.

When the skeleton [Sac] is a monosaccharide, these saccharadic units are used unitarily. In contrast, when the skeleton S is an oligosaccharide or a polysaccharide, they are connected to one another by glycosidic bonds.

According to the invention, when the skeleton [Sac] is an oligosaccharide, it is preferably chosen from among the oligosaccharides having 4 to 9 saccharidic units.

It makes no difference whether the free positions of the saccharadic units of the skeleton [Sac] that do not contain the spacer arm and are not involved in a glycosidic bond are unsubstituted (—H or —OH); or substituted by, for example, an amine function or by a group resulting from the interaction of a hydroxyl function or of an amine function with a protective group such as those traditionally used in organic chemistry and described, for example, in the treatise of T. W. Green et al., "Protective Groups in Organic Synthesis", Third Edition, Wiley Science (1999). Among such protective groups there can be cited in particular the acetyl, benzyl and aryl groups, especially the aryl groups substituted by a radical chosen from among the alkyl chains having 1 to 40 carbon atoms; the 2,2,2-trichloroethyloxycarbonyl (Troc), benzyloxycarbonyl (BzC), trichloroacetamidate (TCA), tert-butyloxycarbonyl (BOC) and fluoranylmethoxycarbonyl (Fmoc) groups as well as the silylated groups, such as, for example, the t-butyldimethylsilyl (tBDMS) and trimethylsilyl (TMS) groups, or else polyethylene glycol (PEG) chains. Advantageously, the presence of an acetyl group may permit better penetration of the substrates into the cells, and the presence of a PEG furthermore makes it possible to adjust the pharmacokinetic properties of the substrates according to the invention.

The subunit or subunits constituting the spacer arm of the enzymatic substrates of formula (I) preferably represent a linear or branched, saturated or unsaturated, substituted or unsubstituted hydrocarbon chain, interrupted and/or terminated by one or more heteroatoms chosen from among N, O and S, and/or by one or more groups chosen from among the $C_1$-$C_4$ alkyl, $C_1$-$C_4$ alkoxy or aryl radicals, or by one or more functions chosen from among the ether, ester, amide, carbonyl, carbamate, urea, thiourea and disulfide functions.

Excluded de facto from this definition are all the spacer arms that would contain (or would be composed of) a phosphate chain, a saccharidic unit or a nitrogen-containing base.

According to a preferred embodiment of the invention, the spacer arm is composed of at least two bifunctional units B1 and B2 such that one of the ends of subunit B1 or respectively B2 is a function that is reactive toward traditional groups for activation of the anomeric position of the saccharidic unit on which they must be fixed (notable examples of groups for activation of the anomeric position: —Br, —SPh with Ph=phenyl; notable example of functions that are reactive toward these activation groups: —OH in particular), the other end of subunit B1 being a function (such as amine or thiol) that is reactive toward a complementary function carried by one of the ends of subunit B2, the said subunit B2 in turn containing, at its other end, a function (such as amine or thiol) that is reactive toward a grafting function attached to the fluorophore group F (such as, for example, an N-hydroxysuccinimidyl, isothiocyanate, sulfotetrafluorophenyl ester (STP ester), maleimide or haloacetamide function).

According to a particularly preferred embodiment of the invention, the spacer arm comprises a subunit B1 chosen from among the monocyclic aromatic groups of the following formula (II):

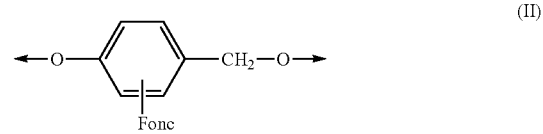

in which:
Fonc is a chemical function that is reactive toward a complementary chemical function of a fluorophore group F or respectively of a group that inhibits the fluorescence of a fluorophore group F,
the arrow starting at the oxygen atom carried directly by the phenyl ring represents the point of attachment of the said subunit B1 to a saccharidic unit of the spacer arm via a covalent bond with the carbon atom situated in anomeric position 1 of the said saccharidic unit,
the arrow starting at the oxygen atom connected to the —CH$_2$— radical represents the point of attachment of the said subunit B1 to a group that inhibits the fluorescence of group F or to a subunit B2 chosen from among the aromatic groups of the following formula (III):

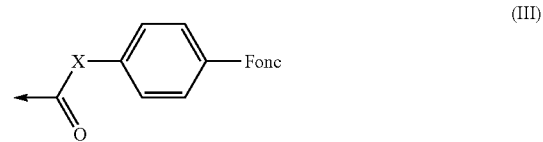

in which:
Fonc is a chemical function that is reactive toward a complementary chemical function of a group that inhibits the fluorescence of the group F or respectively toward a fluorophore group F,
the arrow represents the point of attachment of the said subunit B2 to the subunit B1 via a covalent bond with the oxygen atom of the subunit B1,
X is O, NH or S.

In the subunit B1 of formula (II) hereinabove, the group Fonc is preferably in ortho position relative to the ring carbon atom carrying the oxygen atom.

According to another particularly preferred embodiment of the invention, the spacer arm comprises a subunit B1 chosen from among the monocyclic aromatic groups of the following formula (IV):

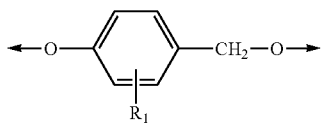

in which:
- $R_1$ is chosen from among the nitro, sulfate and amine groups as well as amine protected by a protective group,
- the arrow starting at the oxygen atom carried directly by the carbon atom of the phenyl ring represents the point of attachment of the said subunit B1 to a saccharidic unit of the spacer arm via a covalent bond with the carbon atom situated in anomeric position 1 of the said saccharidic unit,
- the arrow starting at the oxygen atom attached to the —$CH_2$— radical represents the point of attachment of the said subunit B1 to a subunit B2 chosen from among the groups of the following formula (V):

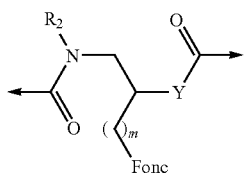

in which:
- $R_2$ is a hydrogen atom or a $C_1$-$C_4$ alkyl radical,
- Fonc is a chemical function that is reactive toward a complementary chemical function of a fluorophore group F or respectively toward a group that inhibits the fluorescence of a fluorophore group F,
- m is an integral number ranging from 1 to 10,
- Y is O, NH or S,
- the arrows represent the point of attachment of the said subunit B2 to subunit B1 on the one hand and to a nitrogen or oxygen atom carried by a subunit B3 of the following formula (VI) on the other hand:

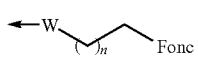

in which:
- W represents O, NH or S,
- the arrows represent the point of attachment of the nitrogen, sulfur or oxygen atom denoted by W via a covalent bond with a carbon atom of the subunit B2,
- n is an integral number ranging from 1 to 10,
- Fonc is a chemical function that is reactive toward a complementary chemical function of a fluorophore group F or respectively toward a group that inhibits the fluorescence of the fluorophore group F.

Thus, according to the nature of the atoms denoted by X, Y and Z, the different subunits of formulas (II) to (VI) capable of constituting the spacer arm of the enzymatic substrates of formula (I) in accordance with the present invention, the spacer arm comprises one or more amide, carbonate, carbamate, urea or thiourea functions that are capable of undergoing spontaneous hydrolysis after enzymatic cleavage of the bond with the saccharidic unit.

More precisely:
- the function interconnecting the subunits B1 of formula (II) and B2 of formula (III) can be a carbonate function (X=O) or a carbamate function (X=NH);
- the function interconnecting the subunits B1 of formula (IV) and B2 of formula (V) is a carbamate function;
- the function interconnecting the subunits B2 of formula (V) and B3 of formula (VI) can be a carbonate (Y=W=O), carbamate (Y=O with W=NH or Y=NH with W=O), urea (Y=W=NH) or else thiourea (Y=S with W=NH or Y=NH with W=S) function.

In the subunits of formulas (II), (III), (V) and (VI), the function Fonc is preferably chosen from among the primary amine and thiol functions.

Among these functions, the primary amine function is particularly preferred.

Among the subunits of formula (II) hereinabove, there are preferred those in which Fonc is situated in ortho position relative to the carbon atom carrying the oxygen atom.

Among the subunits of formula (III) hereinabove, there are preferred those in which:
- X is an oxygen atom and Fonc is a primary amine or thiol function,
- X is a nitrogen atom and Fonc is a primary amine or thiol function.

Among the subunits of formula (IV) hereinabove, there are preferred those in which $R_1$ is situated in ortho position relative to the carbon atom carrying the oxygen atom.

Among the subunits of formula (V) hereinabove, there are preferred those in which:
- $R_2$ is a methyl radical, m=1, Fonc is a primary amine function and Y is an oxygen atom,
- $R_2$ is a methyl radical, m=1, Fonc is a primary amine function and Y=NH.

Among the subunits of formula (VI) hereinabove, there are preferred those in which:
- W is an oxygen atom, n=1, Fonc is a primary amine function and Y is an oxygen atom,
- W represents NH, n=1, Fonc is a primary amine function and Y is an oxygen atom,
- W is a sulfur atom, n=1, Fonc is a primary amine function and Y is an oxygen atom.

According to a particularly preferred embodiment of the invention, the enzymatic substrates of formula (I) according to the invention are chosen from among the compounds of the following formulas (I-1) and (I-2):

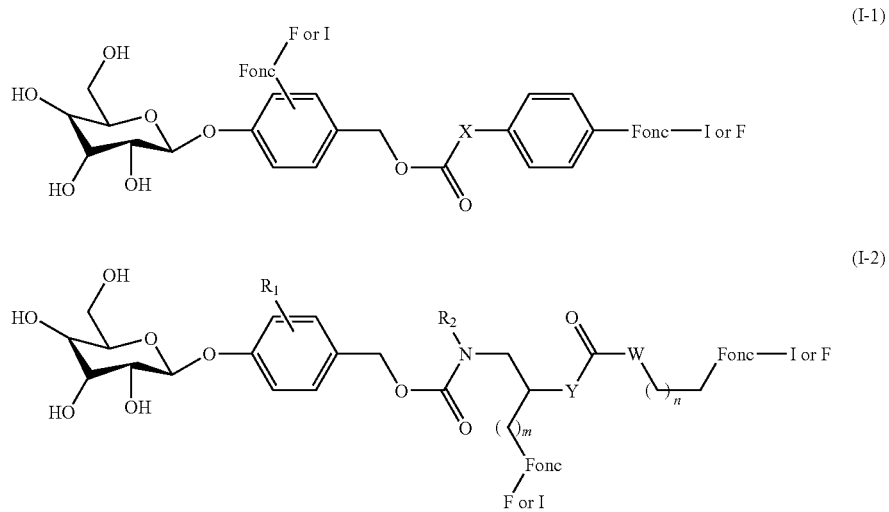

in which F, I, Fonc, X, Y, W, R₁, R₂, m and n have the same meanings as those indicated in the foregoing.

Among the fluorophore groups F, there can be cited in particular fluorescein (sodium fluorescinate) and its derivatives such as fluorescein isothiocyanate (FITC) and 6-carboxyfluorescein (6-Fam); the fluorescent dyes that absorb and emit in the near infrared (NIR), such as those sold under the names Fluorescent Red NIR 700 (excitation wavelength: 672 nm; emission wavelength: 735 nm) and Fluorescent Red NIR 730 (excitation wavelength: 680 nm; emission wavelength: 755 nm) by the Sigma-Aldrich Co.; the fluorescent cyanines, such as Cy5 (n=2) and Cy7 (n=3) (Amersham); 7-hydroxy-9H-(1,3-dichloro-9,9-dimethylacridin-2-one) (DDAO); rhodamine and its derivatives, such as tetramethyl rhodamine isothiocyanate (TRITC); the fluorescent dyes containing reactive amines, such as the coumarins, among which there can be cited in particular the succinimidyl ester of 6-((7-amino-4-methylcoumarin-3-acetyl)amino)hexanoic acid (AMCA); the dipyrromethene boron difluorides sold under the BODIPY® trade names, such as BODIPY® FR—Br₂, BODIPY® R6G, BODIPY® TMR, BODIPY® TR and BODIPY® 530/550 (excitation wavelength/emission wavelength in nm), 558/568, 564/570, 576/589, 581/591, 630/650 and 650/665 sold by Bio-Rad Inc. (USA), IRDye® 800 sold by the LICOR Co. and Alexa Fluor® 750 sold by the Molecular Probes Co.; the porphyrins; the cyanines; the oxazines; the fluorophores derived from pyrene, such as, for example, the Cascade Blue dyes (sold, for example, by Trilink BioTechnologies (USA) or Invitrogen; the diazo derivatives, such as DABCYL®; the dansyl derivatives, such as EDANS® (Eurogentec, Belgium); eosin; erythrosin and the derivatives of sulforhodamine, such as sulforhodamine 101 sulfonyl chloride, also known by the name Texas Red; and fluorescent nanoparticles, or in other words those having emission properties such as "quantum dots", gold nanoparticles, polymer-base nanoparticles and oxide nanoparticles.

According to a particularly preferred embodiment of the invention, the group F is chosen from among the fluorophore groups that absorb and emit in the near infrared, or in other words that absorb and emit at a wavelength ranging between 640 and 900 nm. Among such groups, there can be cited in particular the following fluorophore groups: the fluorescent dyes sold under the names Fluorescent Red NIR 700 (excitation wavelength (Ex.): 672 nm/emission wavelength (Em.): 735 nm) and Fluorescent Red NIR 730 (Ex.: 680 nm/Em.: 755 nm) by the Sigma-Aldrich Co.; Cy5 (n=2; Ex.: 680 nm/Em.: 755 nm), Cy5.5 (Ex.: 675 nm/Em.: 694 nm) and Cy7 (n=3; Ex.: 747 nm/Em.: 775 nm) (Amersham); 7-hydroxy-9H-(1, 3-dichloro-9,9-dimethylacridin-2-one) (DDAO) (Ex.: 646 nm/Em.: 659 nm); IRDye® 800 (Ex.: 778/Em.: 806 nm), Alexa Fluor® 647 (Ex.: 651 nm/Em.: 672 nm), Alexa Fluor® 660 (Ex.: 668 nm/Em.: 698 nm), Alexa Fluor® 680 (Ex.: 684 nm/Em.: 707 nm), Alexa Fluor® (700 (Ex.: 702 nm/Em.: 723 nm) and Alexa Fluor® 750 (Ex.: 749 nm/Em.: 774 nm).

According to a particular embodiment of the invention, the fluorophore group F can be additionally functionalized by one or more amide or urea functions and/or by one or more groups chosen from among the lipophilic chains, the phospholipids and the peptides. When functionalized in this way, the fluorophore groups F exhibit greater affinity for the cells of animal tissues.

According to the invention, group I can be chosen from among all compounds that accept the fluorescence of the group F, or in other words that permit reduction or complete disappearance of the fluorescence of the group F when they both are fixed to the spacer arm of the enzymatic substrates of formula (I). This compound, of diverse natures, can be in particular a chromophore group, a fluorescent or non-fluorescent group or a nanoparticle.

When group I is itself a fluorescent group, then it is chosen from among the groups whose fluorescence inhibits that of the group F. The group I may be identical to the group F (in which case it is said to be self-inhibiting toward fluorescence) and is preferably chosen from among the fluorescent cyanines such as Cy5, Cy5.5 and Cy7, IRDye® 800 and Alexa Fluor®647, 660, 680, 700 and 750. As group I there can also be used a fluorescent group that is different from the group F and that absorbs the fluorescence of the group F by fluorescence resonance energy transfer (FRET). In this case, it is preferable to use the following F/I pairs: Cy5/Cy7 (or Cy7Q); Cy5/Alexa Fluor® 750; Cy7/IRDye® 800; Alexa Fluor® 750/IRDye® 800.

When the group I is a non-fluorescent group, or in other words a fluorescence inhibitor proper ("quencher"), then it is preferably chosen from among the compounds sold under the commercial names DABCYL® and derivatives, Black Hole Quencher® (BHQ) such as BHQ 1, BHQ 2 or BHQ 3 (Biosearch Technologies), Nanogold Particules® (Nanoprobes), Eclipse Dark Quencher® (Epoch Bioscience), Elle Quencher® (Oswell), Cy7Q (Amersham) and the QSY® dyes such as QSY® 7, QSY® 9 and QSY® 21 (Molecular Probes).

Among the enzymatic substrates of formula (I) according to the invention, there are most particularly preferred the compounds of formula (I) in which:

i) the skeleton [Sac] is a galactosamine, the spacer arm is composed of a subunit B1 of formula (II) and of a subunit B2 of formula (III), and F and I are identical. In this case, F and I are chosen, for example, from among the groups Cy5, Cy5.5 and Cy7, Alexa Fluor® 647, 660, 680, 700 and 750, and IRDye® 800, these groups being carried respectively and without difference by the subunits B1 and B2;

ii) the skeleton [Sac] is a galactosamine, the spacer arm is composed of a subunit B1 of formula (IV), of a subunit B2 of formula (V) and of a subunit B3 of formula (VI), and F and I are identical. In this case, F and I are chosen, for example, from among the groups Cy5, Cy5.5 and Cy7, Alexa Fluor® 647, 660, 680, 700 and 750, and IRDye® 800, these groups being carried respectively and without difference by the subunits B2 and B3;

iii) the skeleton [Sac] is a galactosamine, the spacer arm is composed of a subunit B1 of formula (IV) and of a subunit B2 of formula (III), and F and I are different. In this case, F and I are chosen, for example, from among the following pairs of groups: Cy5/Cy7 (or Cy7Q); Cy5/Alexa Fluor® 750; Cy7/IRDye® 800; Alexa Fluor® 750/IRDye® 800, these groups being carried respectively and without difference by the subunits B2 and B3.

According to a particularly preferred embodiment of the invention, the enzymatic substrates of formula (I-1) are chosen from among the following compounds:

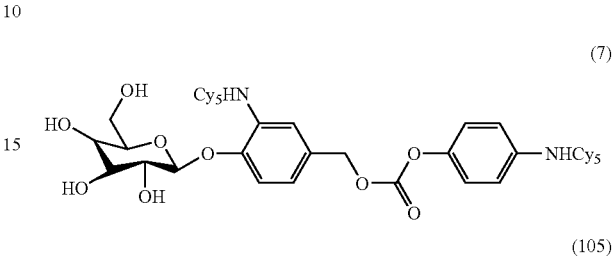

(7)

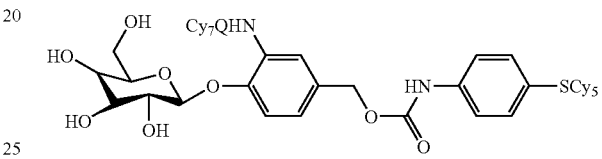

(105)

As enzymatic substrates of formula (I-2), there can be mentioned in particular the following compound:

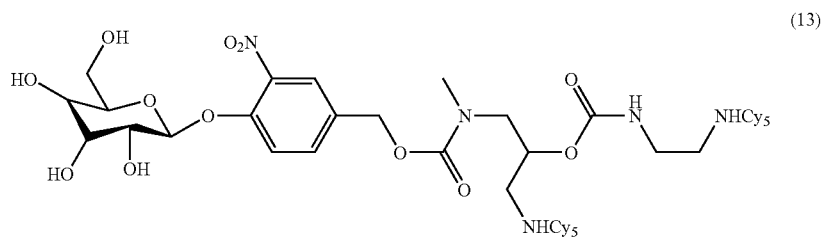

(13)

The enzymatic substrates of formula (I) according to the invention can be prepared easily by carrying out a sequence of separate traditional steps known to the person skilled in the art.

In particular, the enzymatic substrates of formula (I) according to the invention in which the subunits B1 and B2 are chosen respectively from among the subunits of formulas (II) and (III) (compounds of formula (I-1)) and in which F and I represent an identical fluorophore group can be prepared, for example, according to the method (P1) such as represented in the following Scheme D:

SCHEME D

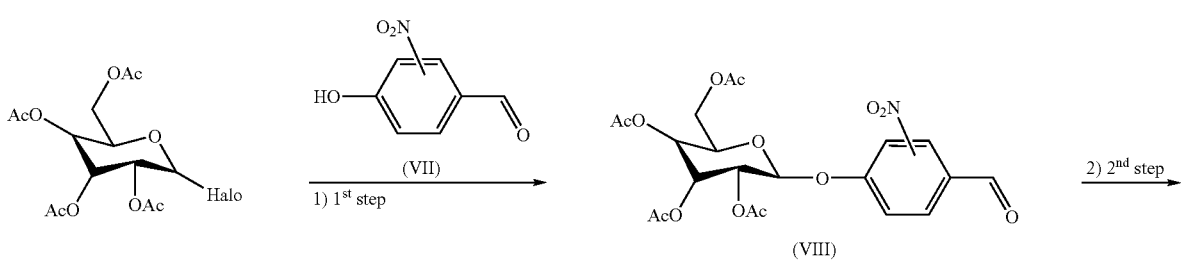

-continued

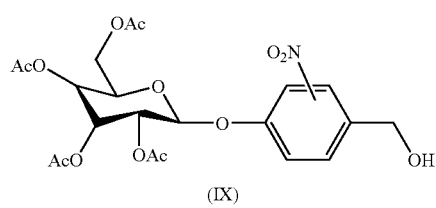
(IX)

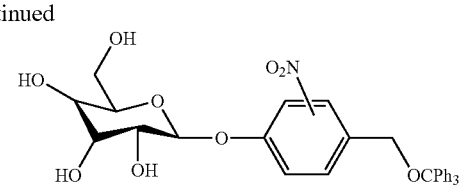
(X)

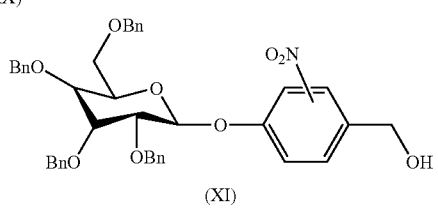
(XI)

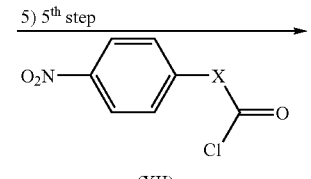
(XII)

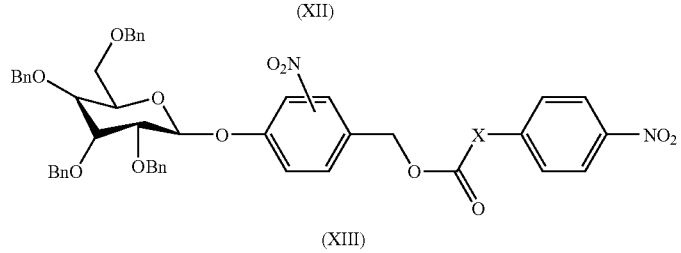
(XIII)

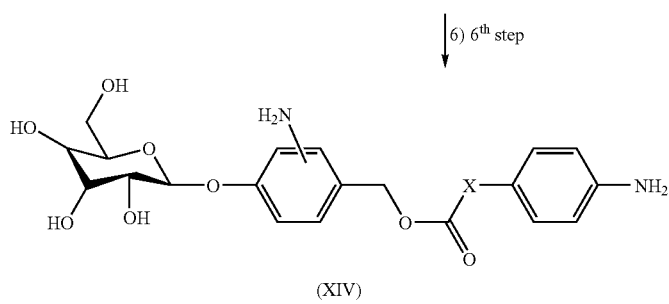
(XIV)

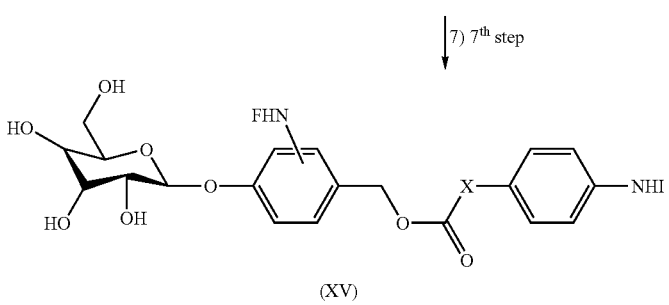
(XV)

according to which:

1) in a first step, a saccharidic skeleton containing at least one saccharidic unit, in which the anomeric position 1 is halogenated and whose hydroxyl functions are acetylated, is reacted in an organic solvent such as, for example, anhydrous acetonitrile, and in the presence of an oxidizing agent, with a 4-hydroxynitrobenzaldehyde of formula (VII), to produce a compound of formula (VIII), in which "Ac" denotes acetyl, its being understood that the nitro group in the compounds of formulas (VII) and (VIII) can occupy any position whatsoever of the benzene ring;

2) in a second step, the compound of formula (VIII) obtained hereinabove in the preceding step is reduced in an organic solvent such as, for example, chloroform, isopropanol or a mixture thereof, in the presence of a reducing agent, to produce a compound of formula (IX);

3) in a third step, the compound of formula (IX) obtained hereinabove in the preceding step is reacted in an organic solvent such as, for example, dichloromethane, with trityl chloride, then the acetyl groups are hydrolyzed to produce a compound of formula (X), in which "Ph" denotes phenyl;

4) in a fourth step, the compound of formula (X) obtained hereinabove in the preceding step is reacted in an organic solvent such as, for example, dimethylformamide, with a benzyl halide, then the trityl group is hydrolyzed to liberate the hydroxyl function and to produce a compound of formula (XI), in which "Bn" denotes benzyl;

5) in a fifth step, the compound of formula (XI) obtained hereinabove in the preceding step is reacted in an organic solvent such as dichloromethane, with a compound of formula (XII), to produce a compound of formula (XIII), in which "Bn" denotes benzyl; its being understood that X represents O or NH in the compounds of formulas (XII) and (XIII);

6) in a sixth step, the nitro groups of the compound of formula (XIII) obtained hereinabove in the preceding step are reduced in the presence of a reducing agent to produce a compound of formula (XIV); and 7) in a seventh step, the compound of formula (XIV) obtained hereinabove in the preceding step is reacted in an organic solvent such as, for example, anhydrous dimethylformamide, with a fluorophore compound previously functionalized by an NHS group, to produce a compound of formula (XV), in which F=I (compound of type (I-1)).

On the other hand, the enzymatic substrates of formula (I) according to the invention, in which the spacer arm comprises at least one subunit B1 of formula (IV), a subunit B2 of formula (V) and a subunit B3 of formula (VI) (compounds of formula (I-2)), and in which F and I represent an identical fluorophore group, can be prepared, for example, according to the method (P2) such as represented in the following scheme E:

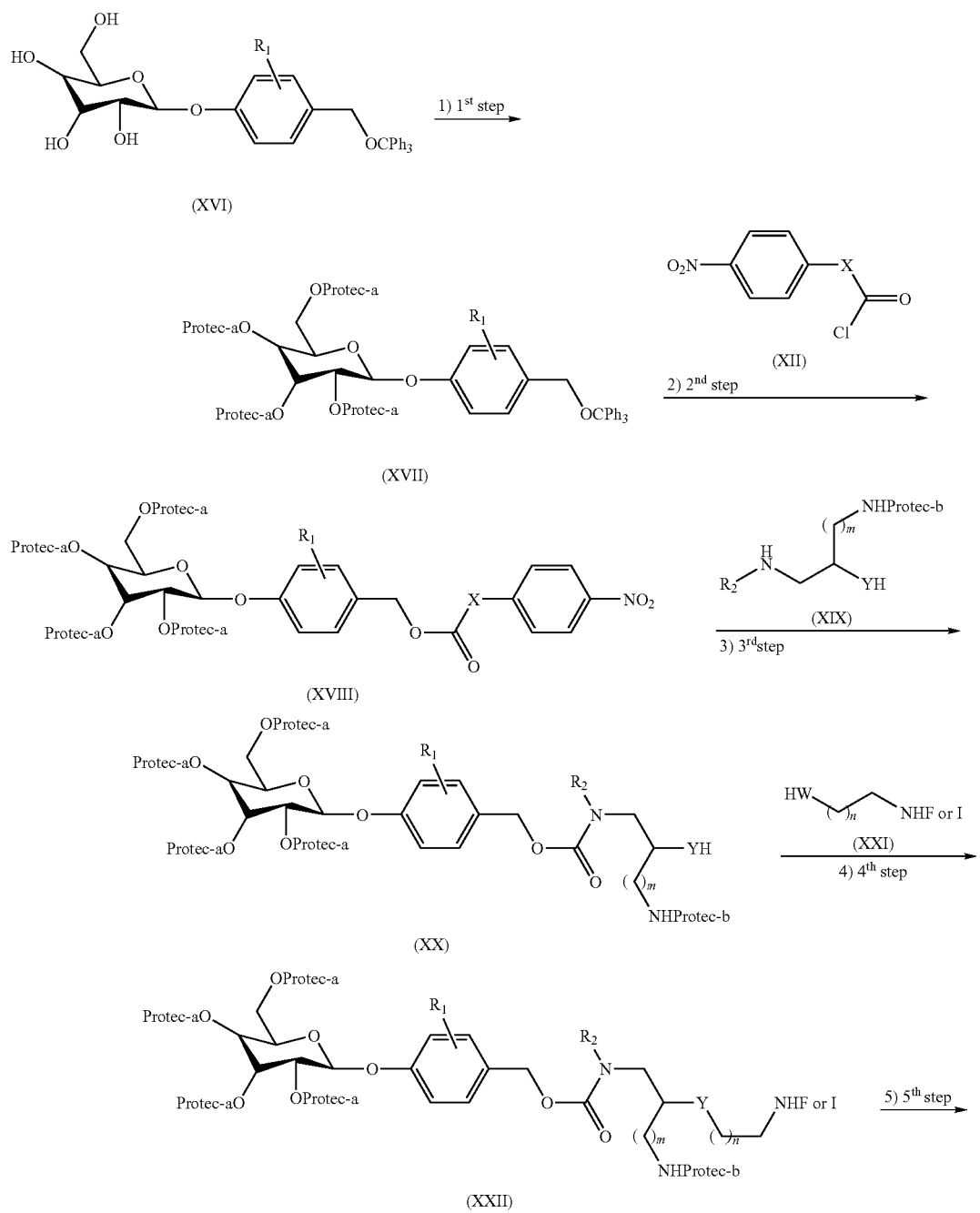

-continued

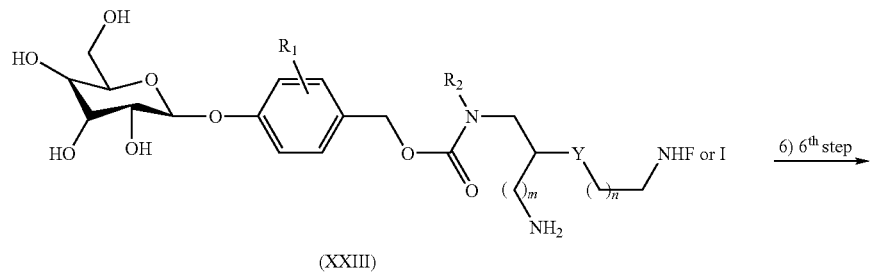

(XXIII)

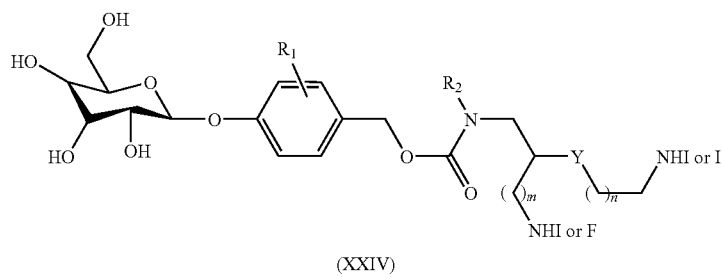

(XXIV)

according to which:

1) in a first step, a compound of formula (XVI), in which R₁ has the same meaning as that indicated in the foregoing for the subunit B1 of formula (IV) and "Ph" denotes phenyl, is reacted in an organic solvent such as, for example, dichloromethane, with a protective groups "Protec-a" such as, for example, tert-butyldimethylchlorosilane (TBDMS) in the presence of an imidazole compound to produce a compound of formula (XVII);

2) in a second step, the compound of formula (XVII) obtained hereinabove in the preceding step is reacted in an organic solvent such as, for example, dichloromethane, with a compound of formula (XII) such as defined hereinabove in the fifth step of the method P1, to produce a compound of formula (XVIII);

3) in a third step, the compound of formula (XVIII) obtained hereinabove in the preceding step is reacted in an organic solvent such as, for example, dichloromethane, with a compound of formula (XIX), in which R₂, Y and m have the same meanings as those indicated in the foregoing for the subunit B2 of formula (V) and Protec-b is a protective group such as, for example, Fmoc to produce a compound of formula (XX);

4) in a fourth step, the compound of formula (XX) obtained hereinabove in the preceding step is reacted in an organic solvent such as, for example, anhydrous dichloromethane, with a compound of formula (XXI), in which W, F, I and n have the same meanings as those indicated in the foregoing for the subunit B3 of formula (VI), to produce a compound of formula (XXII);

5) in a fifth step, the compound of formula (XXII) obtained hereinabove in the preceding step is completely deprotected in an organic solvent such as, for example, anhydrous dichloromethane, in the presence of piperidine then tetrabutylammonium fluoride, to produce a compound of formula (XXIII);

6) in a sixth step, the compound of formula (XXIII) obtained hereinabove in the preceding step is reacted in an organic solvent such as, for example, anhydrous DMF, with a compound F or I respectively, previously functionalized by an NHS group, to produce a compound of formula (XXIV) (compound of type (I-2)).

Methods P1 and P2 represented in schemes D and E hereinabove comprise a minimal number of steps. It must nevertheless be understood that, depending on the nature of the enzymatic substrate of formula (I-1) or (I-2) to be obtained, additional protection/deprotection reactions may be necessary, particularly if method P1 or P2 respectively is to be applied to enzymatic substrates of formula (I-1) or (I-2) respectively, in which F and I are different. These reactions are carried out in traditional manner using methods known to the person skilled in the art.

As an additional example, the compounds of formula (I-1) in which F and I are different and X=NH can be prepared in particular according to the method P3 such as represented in the following scheme F:

SCHEME F

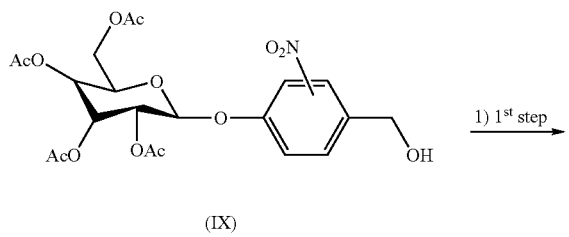

(IX)

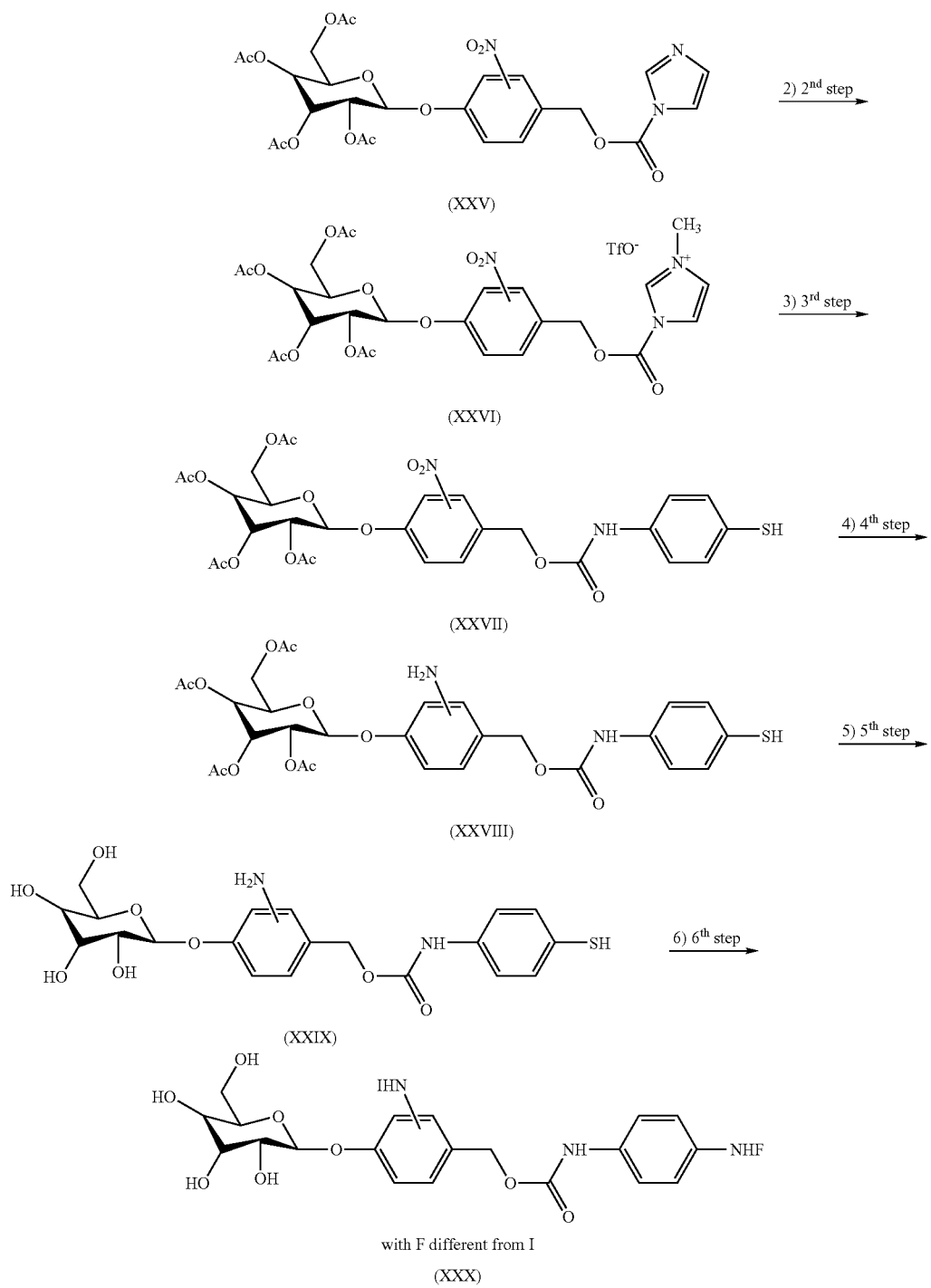

according to which:

1) in a first step, a compound of formula (IX) such as defined in step 2) of method P1 is reacted in an organic solvent such as, for example, dichloromethane, with 4-(dimethylamino)pyridine (DMAP), in the presence of carbonyl diimidazole, to produce a compound of formula (XXV), in which "Ac" denotes acetyl;

2) in a second step, the compound of formula (XXV) obtained hereinabove in the preceding step is reacted in an organic solvent such as, for example, dichloromethane, with methyl trifluoromethanesulfonate, to produce a compound of formula (XXVI);

3) in a third step, the compound of formula (XXVI) obtained hereinabove in the preceding step is reacted in an organic solvent such as, for example, dichloromethane, with 4-aminothiophenol, to produce a compound of formula (XXVII);

4) in a fourth step, the compound of formula (XXVII) obtained hereinabove in the preceding step is reduced in an organic solvent such as, for example, methanol, in the presence of a reducing agent, to produce a compound of formula (XXVIII);

5) in a fifth step, the acetyl groups of the compound of formula (XXVIII) are hydrolyzed in an organic solvent such as methanol in the presence, for example, of sodium methylate, to produce a compound of formula (XXIX); and 6) in a sixth step, the compound of formula (XXIX) obtained hereinabove in the preceding step is reacted in an organic solvent such as, for example, anhydrous dimethylformamide, with a fluorophore compound previously functionalized by a maleimide group and a compound that inhibits the fluorescence of the fluorophore group, the said inhibitor compound having been previously functionalized by an NHS group, in the presence of diethylamine, to produce a compound of formula (XXX), in which F is different from 1 (compound of type (I-1)).

In each step of these methods P1, P2 and P3, the intermediate compounds and the final compound(s) at the end of synthesis are preferably washed, isolated and purified according to methods traditionally used for this purpose, such as, for example, purification on a silica gel column.

Thus, as has been amply described and explained in the foregoing, the enzymatic substrates of formula (I) according to the invention can be used for detection of enzymatic activity in vitro and in vivo.

The present invention therefore has as a second object the use of at least one enzymatic substrate of formula (I) such as defined in the foregoing as a fluorescent reagent for detection of enzymatic activity in vitro.

According to a particularly preferred embodiment, the fluorophore group F of the enzymatic substrates of formula (I) is chosen from among the groups that absorb and emit in the near infrared, particularly between 640 and 900 nm, in order to permit use in vivo. In this case, the present invention also has as an object the use of at least one enzymatic substrate of formula (I), in which the fluorophore group F is chosen from among the groups that absorb and emit in the near infrared, for preparation of a diagnostic reagent intended for functional imaging in vivo and in particular for imaging, by fluorescence, the expression of the reporter genes lacZ and gusA of E. coli.

Finally, the invention has as an object a diagnostic reagent, characterized in that it comprises at least one solution composed of water or of a mixture of water and at least one organic solvent, the said solution containing at least one enzymatic substrate of formula (I) as defined in the foregoing.

According to a particular and preferred embodiment of the invention, the reagent is an in vivo diagnostic reagent and the enzymatic substrate of formula (I) comprises at least one fluorophore group F chosen from among the fluorophore groups that absorb and emit in the near infrared.

As usable organic solvents there can be cited the solvents traditionally used for preparation of diagnostic reagents, including, for example, the lower alcohols, such as ethanol, and dimethyl sulfoxide (DMSO). When they are used, these solvents can represent up to 50% (by volume) of the solution containing the enzymatic substrate of formula (I).

According to a particular embodiment of the invention, the solution can additionally contain a physiologically acceptable buffer, such as a phosphate buffer, an example being PBS ("phosphate buffer saline") at pH 7.2.

Within the diagnostic reagent according to the invention, the concentration of the enzymatic substrate or substrates of formula (I) preferably ranges between 1 µM and approximately 1 mM, more preferably between 10 µM and approximately 200 µM. According to a particularly preferred embodiment of the invention, this concentration is approximately 100 µM.

In addition to the foregoing provisions, the invention further comprises other provisions that will become clear from the rest of the description hereinafter, which relates to preparation examples of examples of synthesis of enzymatic substrates of formula (I), as well as to the attached drawings, wherein:

FIG. 1 illustrates the functional principle of an enzymatic substrate of type (I-1). In this figure, F, I, Fonc and X are as defined in the foregoing; each of the two groups F and I is grafted onto separate aromatic rings on one side or the other of carbonate or carbamate functions, although the two positions can nevertheless be interchanged. The enzymatic cleavage liberates the self-cleavable arm of the sugar, which then hydrolyzes spontaneously into two distinct subunits, each carrying one of the two groups F or I. Since from that point on the two groups F and I are at a distance from one another, the group F is able to emit fluorescence.

Figure 2:
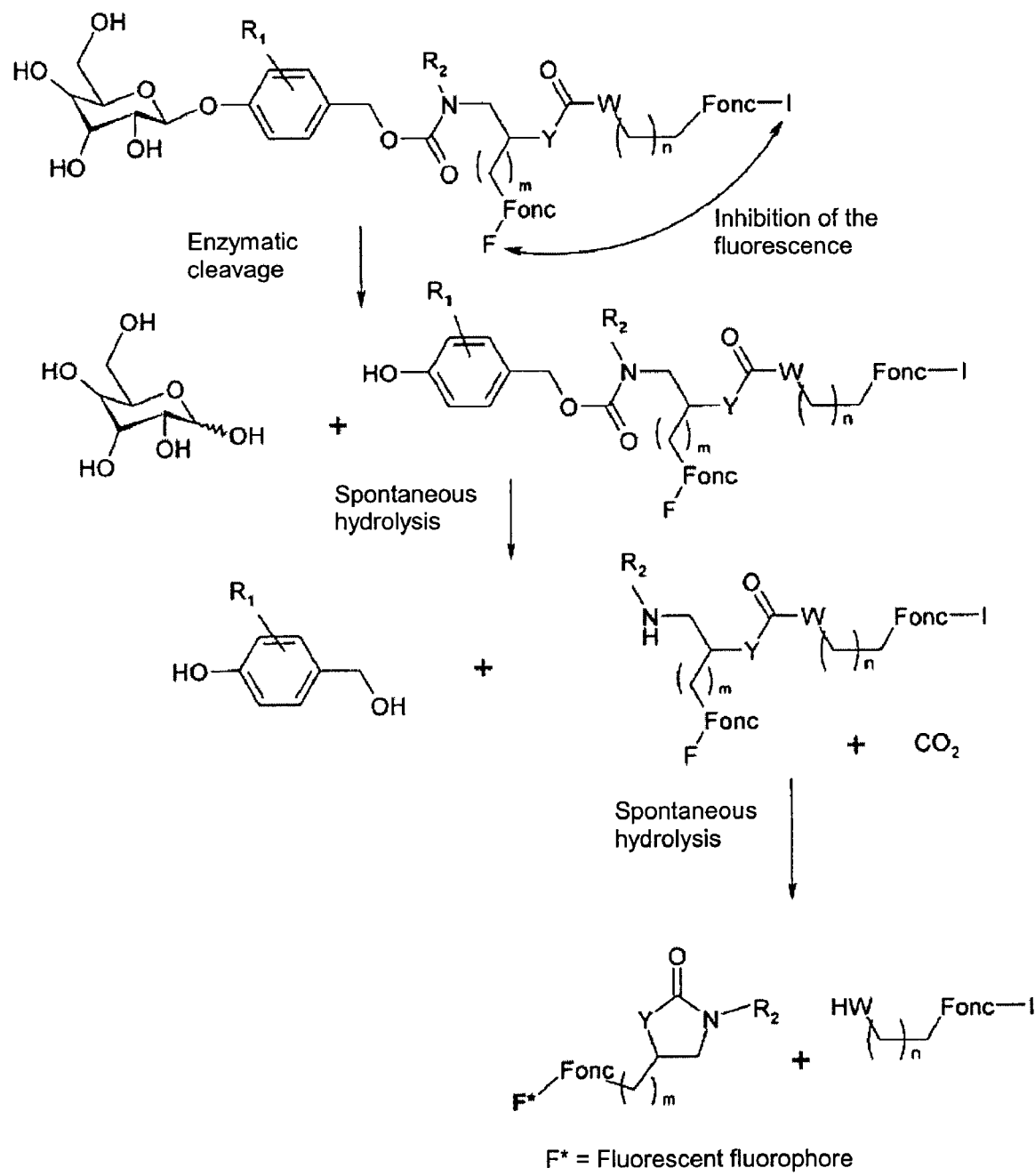
FIG. 2 shows the functionality and mode of operation of a second embodiment of the present invention.

FIG. 2 illustrates the functional principle of an enzymatic substrate of (I-2). In this figure, F, I, Fonc, $R_1$, $R_2$, Y, W, m and n are as defined in the foregoing. Each of the two groups F and I is grafted onto one side or the other of carbonate, carbamate or urea functions. Nevertheless, the two positions may be interchanged. The enzymatic cleavage liberates the self-cleavable arm of the sugar, which hydrolyzes spontaneously into two distinct subunits, one aromatic and the other still containing the two groups F and I. A final spontaneous intramolecular reaction causes separation of the two groups F and I at the position of the carbonate, amide or else urea function. Since from that point on the two groups F and I are at a distance from one another, the group F is then able to emit fluorescence.

It must be clearly understood, however, that the examples hereinafter are given only by way of illustration of the invention and furthermore are in no case to be construed as a limitation thereof.

EXAMPLE 1

Synthesis of an Enzymatic Substrate According to the Invention in which F=I=CY5 and X=O(Compound of Formula (I-1)

In this example, the following compound (7) was synthesized:

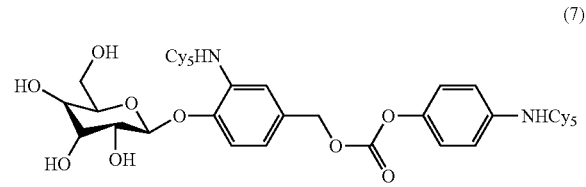

(7)

1) First Step: Synthesis of the Intermediate (1)

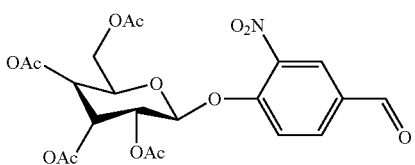

(1)

To a solution of α-D-acetobromogalactose (10 g, 24.3 mmol) in anhydrous acetonitrile (100 mL), there were added 6.9 g (41.3 mmol) of 4-hydroxy-3-nitrobenzaldehyde and 19.7 g (85.1 mmol) of silver oxide. The reaction mixture was agitated at room temperature under an argon atmosphere and shielded from light for 12 hours. Then the mixture was filtered over silica and the filtrate was concentrated under reduced pressure. In this way there was obtained 7.44 g of the intermediate (1) in the form of a pale yellow solid (yield: 62%). The product was then used directly in the following step, without additional purification.

2) Second Step: Synthesis of the Intermediate (2)

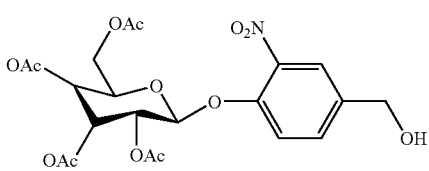

(2)

To a solution of 7.44 g (14.9 mmol) of the intermediate (2) obtained hereinabove in the preceding step in 160 mL of a mixture of trichloromethane and isopropanol (CHCl$_3$/iPrOH: 3/1, v/v), cooled to 0° C. under an argon atmosphere, there was added 6.8 g (180 mmol) of sodium borohydride in small portions. After 12 hours of agitation at room temperature, the reaction mixture was hydrolyzed by a saturated sodium hydrogen carbonate solution. The aqueous phase was extracted two times with 300 mL of dichloromethane; the organic phase obtained was washed two times with 200 mL of water, dried over magnesium sulfate, filtered over sintered glass then concentrated under reduced pressure. In this way there was obtained 5.86 g of the expected intermediate (2) in the form of a pale yellow solid (yield: 78%). The product was then used directly in the following step, without additional purification.

3) Third Step: Synthesis of the Intermediate (3)

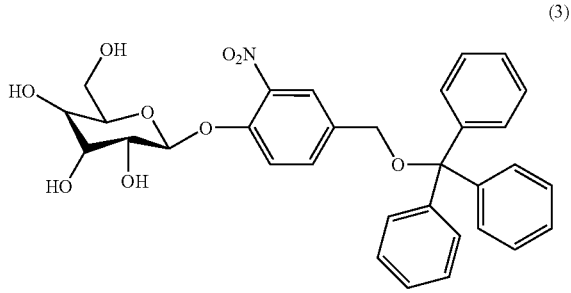

(3)

To a solution of 1.03 g (2.05 mmol) of the intermediate (2) obtained hereinabove in the preceding step in 20 mL of dichloromethane, there were added 1.72 g (6.17 mmol) of trityl chloride, 860 μL (6.17 mmol) of triethylamine and 25 mg (0.205 mmol) of 4-(dimethylamino)pyridine (DMAP). The reaction mixture was agitated for 12 hours at room temperature before being purified directly by chromatography on a silica gel column using a mixture of ethyl acetate, heptane and triethylamine (AcOEt/heptane/Et$_3$N: 20/79/1, v/v/v) as liquid phase. In this way there was obtained 1.18 g of a beige solid (yield: 77%).

To a solution of 1.18 g (1.59 mmol) of this product in 16 mL of anhydrous methanol, there was added 86 mg (1.59 mmol) of sodium methylate. The reaction mixture was stirred at room temperature for 12 hours, before being acidified to pH=5 with Dowex® H$^+$ resin. After filtration then concentration under reduced pressure, there was obtained 839 mg of the intermediate (3) in the form of a yellow solid (yield: 92%). The product was then used directly in the following step, without additional purification.

4) Fourth Step: Synthesis of the Intermediate (4)

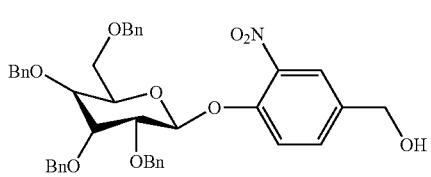

(4)

in which "Bn" denotes benzyl.

To a solution, cooled to 0° C. under an argon atmosphere, of 839 mg (1.46 mmol) of the intermediate (4) obtained hereinabove in the preceding step in 15 mL of anhydrous dimethylformamide (DMF), there was added 351 mg (8.77 mmol) of 60% sodium hydride. After 10 minutes of agitation, there was then added 1.39 mL (11.7 mmol) of benzyl bromide. The reaction mixture was agitated at room temperature for 12 hours, before being hydrolyzed. After partition with H$_2$O and AcOEt, the aqueous phase was extracted two times with 150 mL of ethyl acetate; the organic phase obtained was washed two times with 100 mL of a saturated aqueous sodium chloride solution, dried over magnesium sulfate, filtered over sintered glass then concentrated under reduced pressure. The residue was purified by chromatography on silica gel, using a mixture comprising AcOEt/heptane/Et$_3$N: 10/89/1, v/v/v as liquid phase. There was obtained 888 mg of a yellow oil (yield: 65%).

To a solution, cooled to 0° C. under an argon atmosphere, of 888 mg (0.951 mmol) of this product in 5 mL of dichloromethane, there was then added 71 μL (0.951 mmol) of trifluoroacetic acid. The reaction mixture was agitated at 0° C. for 1 hour, before being neutralized by an aqueous sodium hydrogen carbonate solution. The aqueous phase was extracted two times with 150 mL of dichloromethane; the organic phase obtained was washed two times with 100 mL of water, dried over magnesium sulfate, filtered over sintered glass then concentrated under reduced pressure. The residue obtained in this way was purified by chromatography on silica gel (AcOEt/heptane: 40/60, v/v) to produce 605 mg of the expected intermediate (4) in the form of a pale yellow oil (yield: 92%).

5) Fifth Step: Synthesis of the Intermediate (5)

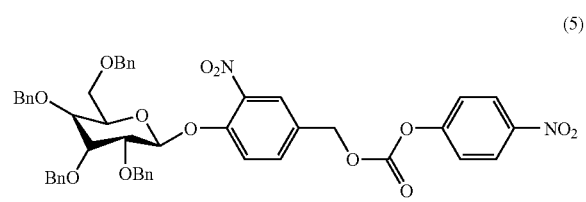

(5)

To a solution of 233 mg (0.337 mmol) of the intermediate (4) obtained hereinabove in the preceding step in 2 mL of dichloromethane, there were added 94 µL (0.674 mmol) of triethylamine and 102 mg (0.505 mmol) of 4-nitrophenyl chloroformate. The reaction mixture was agitated at room temperature for 12 hours, before being hydrolyzed with an aqueous sodium hydrogen carbonate solution. The aqueous phase was extracted two times with 50 mL of dichloromethane; the organic phase obtained was washed two times with 25 mL of water, dried over magnesium sulfate, filtered over sintered glass then concentrated under reduced pressure. The residue was purified by chromatography on silica gel (AcOEt/heptane: 15/85 v/v) to produce 213 mg of the expected intermediate (5) in the form of a yellow oil (yield: 74%).

6) Sixth Step: Synthesis of the Intermediate (6)

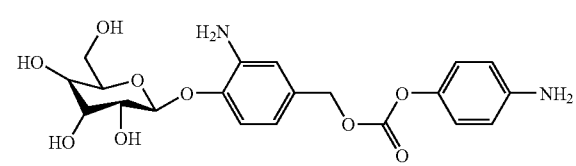

(6)

To a solution of 165 mg (0.192 mmol) of the intermediate (5) obtained hereinabove in the preceding step in 2 mL of methanol, there was added 17 mg of palladium on charcoal having a moisture content of 10%. The reaction mixture was purged with molecular hydrogen five times, before being agitated at room temperature for 12 hours. After filtration over celite and concentration under reduced pressure, there was obtained 78 mg of the intermediate compound (6) in the form of a yellow oil (yield: 93%). The product was then used directly in the following step, without additional purification.

7) Seventh Step: Synthesis of the Compound (7) According to the Invention

To a solution of 5 mg (5.7 µmol) of Cy5-NHS (GE Amersham) in 500 µL of anhydrous DMF under an argon atmosphere, there were added 250 µL of diethylamine and 1.3 mg (2.93 µmol) of the intermediate (6) obtained hereinabove in the preceding step. The reaction mixture was agitated at room temperature for 12 hours, before being concentrated under reduced pressure. After purification by HPLC, the expected enzymatic substrate (7) was obtained in a yield of 72%.

EXAMPLE 2

Synthesis of an Enzymatic Substrate According to the Invention in which F=I=Cy5 and X=Y=O, m=n=1 (Compound of Formula (I-2)

In this example, the following compound (13) was synthesized:

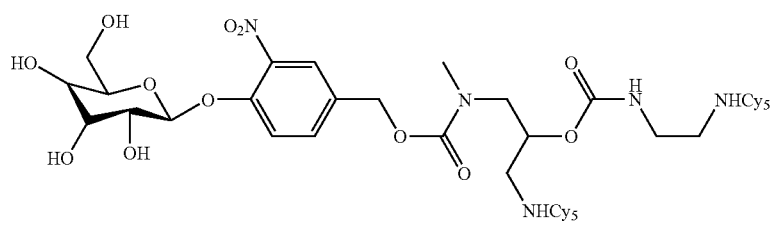

(13)

1) First Step: Synthesis of the Intermediate (8)

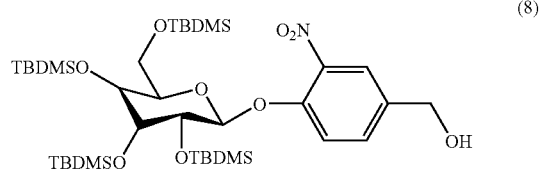

(8)

in which "TBDMS" represents the protective group tert-butyldimethylsilane.

To a solution of 1.21 g (2.11 mmol) of the intermediate (3) such as obtained hereinabove at the end of the third step of Example 1 in 11 mL of dichloromethane, there were added 862 mg (12.7 mmol) of imidazole and 1.9 g (12.7 mmol) of tert-butyldimethylchlorosilane. The reaction mixture was agitated at room temperature for 12 hours, before being hydrolyzed with a saturated aqueous sodium hydrogen carbonate solution. The aqueous phase was extracted two times with 150 mL of dichloromethane; the organic phase obtained was washed two times with 100 mL of water, dried over magnesium sulfate, filtered over sintered glass then concentrated under reduced pressure. The residue was purified by chromatography on silica gel (AcOEt/heptane: 20/80, v/v) to produce 1.57 g of a product having the form of a yellow oil (yield: 72%).

To a solution, cooled to 0° C. under an argon atmosphere, of 1.57 g (1.52 mmol) of this product in 8 mL of dichloromethane, there was added 113 µL (1.52 mmol) of trifluoroacetic acid. The reaction mixture was agitated at 0° C. for 1 hour, before being neutralized by an aqueous sodium hydrogen carbonate solution. The aqueous phase was extracted two times with 150 mL of dichloromethane; the organic phase obtained was washed two times with 100 mL of water, dried over magnesium sulfate, filtered over sintered glass then concentrated under reduced pressure. The residue was purified by chromatography on silica gel (AcOEt/heptane: 40/60, v/v). 1.05 g of yellow oil was obtained (yield: 88%).

2) Second Step: Synthesis of the Intermediate (9)

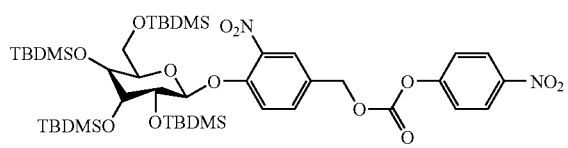

(9)

To a solution of 1.0 g (1.27 mmol) of the intermediate (8) obtained hereinabove in the preceding step in 6 mL of dichloromethane, there were added 354 µL (2.54 mmol) of triethylamine and 384 g (1.90 mmol) of 4-nitrophenyl chloroformate. The reaction mixture was agitated at room temperature for 12 hours, before being hydrolyzed with an aqueous sodium hydrogen carbonate solution. The aqueous phase was extracted two times with 150 mL of dichloromethane; the organic phase obtained was washed two times with 100 mL of water, dried over magnesium sulfate, filtered over sintered glass then concentrated under reduced pressure. The residue was purified by chromatography on silica gel (AcOEt/heptane: 15/85 v/v) to produce 919 mg of the intermediate compound (9) in the form of a yellow oil (yield: 76%).

3) Third Step: Synthesis of the Intermediate (10) (X=O, m=1)

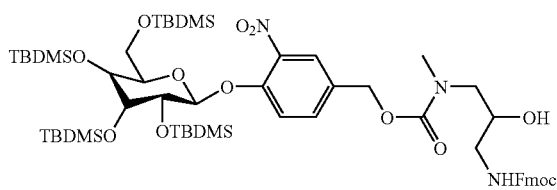

in which Fmoc is the protective group fluorenylmethyloxycarbonyl.

To a solution of 278 mg (0.295 mmol) of the intermediate (9) obtained hereinabove in the preceding step in 1.5 mL of dichloromethane, there was added 114 mg (0.350 mmol) of (9H-fluoren-9-yl)methyl-2-hydroxy-3-(methylamino)propylcarbamate. After 12 hours of agitation at room temperature, the reaction mixture was hydrolyzed with a saturated sodium hydrogen carbonate solution. The aqueous phase was extracted two times with 50 mL of dichloromethane; the organic phase obtained was washed two times with 30 mL of water, dried over magnesium sulfate, filtered over sintered glass then concentrated under reduced pressure. There was obtained 226 mg of intermediate compound (10) in the form of a yellow oil (yield: 68%). The product was then used directly in the following step, without additional purification.

4) Fourth Step: Synthesis of the Intermediate 11 (X=O, Y=N, B=Cy5 m=n=1)

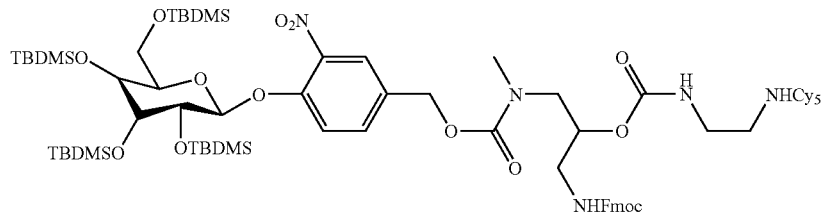

To a solution, cooled to 0° C. under an argon atmosphere, of 212 mg (0.186 mmol) of the intermediate compound (10) obtained hereinabove in the preceding step in 2 mL of anhydrous dichloromethane, there was added 22 mg (0.223 mmol) of phosgene. The reaction mixture was agitated for 1 hour at 0° C., before the addition of 165 mg (0.372 mmol) of the compound having the following formula: $H_2N$—$(CH_3)_2$—NHCy5. The reaction mixture was agitated at room temperature for 2 hours, before being concentrated under reduced pressure. There was obtained 14 mg of a residue, which was then purified by HPLC to produce 11.3 mg of the expected intermediate compound (11).

5) Fifth Step: Synthesis of the Intermediate (12) (X=O, Y=N, B=Cy5, m=n=1)

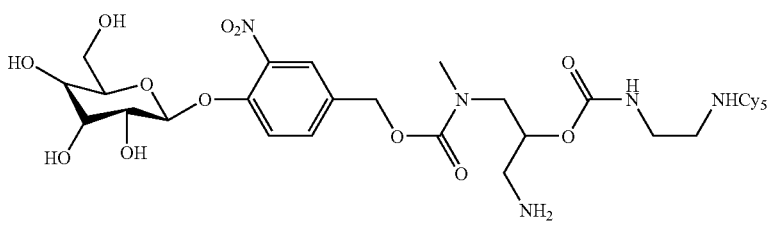

To a solution of 11.3 mg (5.9 µmol) of the intermediate compound (11) obtained hereinabove in the preceding step in 1 mL of anhydrous dichloromethane, there was added 1.16 µL (11.8 µmol) of piperidine. The reaction mixture was agitated for 2 hours, and then there was added 23.6 µL (23.6 µmol) of a 1.0 M solution of tetrabutylammonium fluoride in tetrahydrofuran (THF). The reaction mixture was agitated for 4 hours, before being concentrated under reduced pressure. The residue was then purified by HPLC to produce 8.7 mg of the intermediate compound (12).

6) Sixth Step: Synthesis of the Compound (13)

To a solution of 6.7 mg (7.6 µmol) of Cy5-NHS in 500 µL of anhydrous DMF under an argon atmosphere, there were added 250 µL of diethylamine and 4.8 mg (3.8 µmol) of the intermediate (12) obtained hereinabove in the preceding step. The reaction mixture was agitated at room temperature for 12 hours, before being concentrated under reduced pressure. After purification by HPLC, there was obtained 4.4 mg of the expected compound of formula (13).

EXAMPLE 3

Synthesis of an Enzymatic Substrate According to the Invention in which F=Cy5, I=Cy7Q AND X=NH (Compound of Formula (I-1)

In this example, the following compound (105) was synthesized:

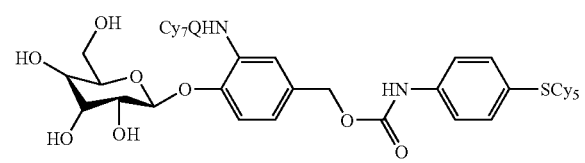
(105)

1) First Step: Synthesis of the Intermediate (100)

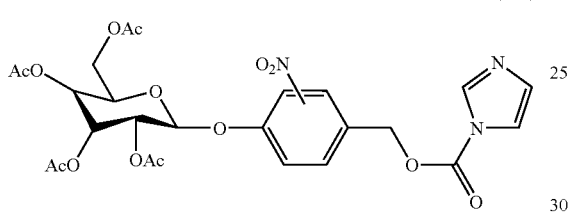
(100)

To a solution of the intermediate (2) such as obtained hereinabove at the end of the second step of Example 1 (1.0 g, 2.0 mmol) in 15 mL of dichloromethane, there were added 49 mg (0.4 mmol) of DMAP and 650 mg (4.0 mmol) of carbonyl diimidazole. The reaction mixture was agitated at room temperature for 12 hours, before being concentrated under reduced pressure. The oil obtained was purified by chromatography on silica gel (AcOEt/heptane: 50/50, v/v then 70/30, v/v and 100/0, v/v). In this way there was obtained 702 mg of the intermediate (100) in the form of a white foam (yield: 59%).

2) Second Step: Synthesis of the Intermediate (101)

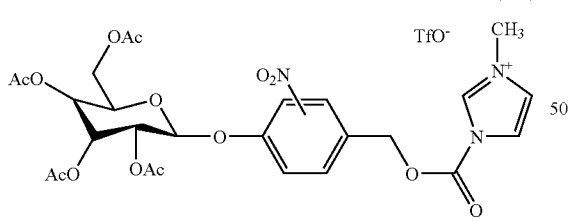
(101)

To a solution of 700 mg (1.18 mmol) of the intermediate (100) obtained hereinabove in the preceding step in 8 mL of anhydrous dichloromethane, and under an argon atmosphere, there was added 267 μL (2.36 mmol) of methyl trifluoromethanesulfonate. The reaction mixture was agitated for 10 minutes at room temperature, before being concentrated under reduced pressure. The residue was triturated several times in diethyl ether before being dried under vacuum. In this way there was obtained 822 mg of the expected intermediate (101) in the form of a white solid (yield: 92%). The product was then used directly in the following step, without additional purification.

3) Third Step: Synthesis of the Intermediate (102)

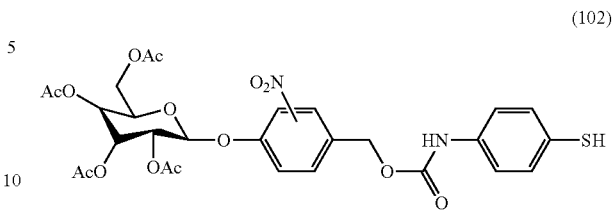
(102)

To a solution of 700 mg (0.924 mmol) of the intermediate (101) obtained hereinabove in the preceding step in 5 mL of anhydrous dichloromethane, and under an argon atmosphere, there was added 231 mg (1.85 mmol) of 4-aminothiophenol. The reaction mixture was agitated for 2 hours at room temperature, before being concentrated under reduced pressure. The oil obtained was purified by chromatography on silica gel (AcOEt/heptane: 30/70, v/v). In this way there was obtained 457 mg of the expected intermediate compound (102) in the form of a pale yellow solid (yield: 76%).

4) Fourth Step: Synthesis of the Intermediate (103)

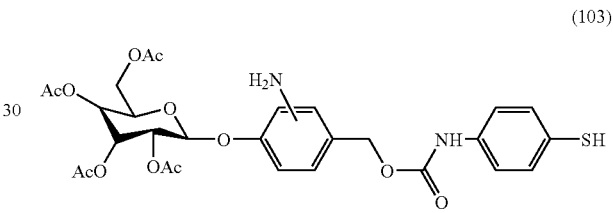
(103)

To a solution of 330 mg (0.507 mmol) of the intermediate (102) obtained hereinabove in the preceding step in 3 mL of methanol and 500 μL of concentrated hydrochloric acid, there was added 192 mg (1.01 mmol) of tin dichloride. The reaction mixture was then agitated for 12 hours at room temperature. After partition with dichloromethane and water, the pH of the mixture was raised to 8-9 by adding a saturated aqueous sodium hydrogen carbonate solution. The aqueous phase was extracted two times with dichloromethane, dried over magnesium sulfate, filtered over sintered glass then concentrated under reduced pressure. The residue was purified by chromatography on silica gel (AcOEt/heptane: 70/30, v/v). There was obtained 226 mg of the expected intermediate (103) in the form of a yellow oil (yield: 72%).

5) Fifth Step: Synthesis of the Intermediate (104)

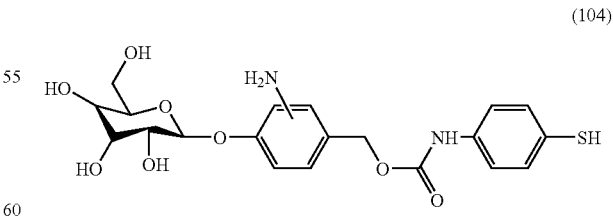
(104)

To a solution of 210 mg (0.338 mmol) of the intermediate (103) obtained hereinabove in the preceding step in 3 mL of anhydrous methanol, there was added 18 mg (0.338 mmol) of sodium methylate. The reaction mixture was agitated at room temperature for 12 hours, before being acidified to pH 7 with Dowex® H⁺ resin. After filtration then concentration under reduced pressure, there was obtained 145 mg of the expected intermediate (104) in the form of a yellow solid (yield: 95%). The product was then used directly in the following step, without additional purification.

6) Sixth Step: Synthesis of the Compound (105) According to the Invention

To a solution of 24 mg (26.5 μmol) of Cy7Q-NHS and 20 mg of Cy5-maleimide in 1 mL of anhydrous DMF under an argon atmosphere, there were added 500 μL of diethylamine and 10 mg (22.1 μmol) of the intermediate (104) obtained hereinabove in the preceding step. The reaction mixture was agitated at room temperature for 12 hours, before being concentrated under reduced pressure. After purification by preparative HPLC, there was obtained 26 mg of the expected compound (105) (yield: 62%).

EXAMPLE 4

Synthesis of an Enzymatic Substrate According to the Invention in which F=Cy5, I=FluoQuench 661, $R_1$=NO$_2$, $R_2$=H, Y=O, W=N and m=n=1

(Compound of Formula (I-2))

In this example, the following compound (200) was synthesized:

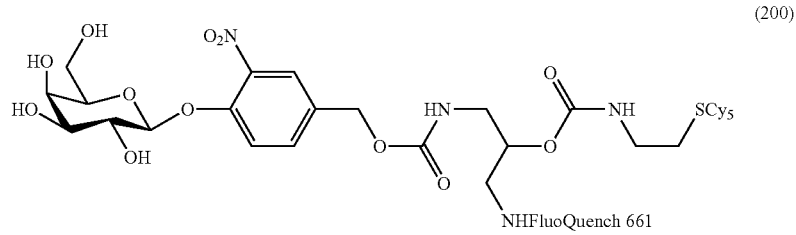

(200)

1) First Step: Synthesis of the Intermediate (201)

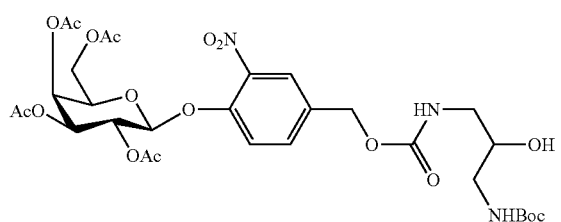

(201)

To a solution of 700 mg (0.924 mmol) of the intermediate (101) such as obtained hereinabove at the end of the second step of Example 3 in 5 mL of anhydrous N,N-dimethylformamide and under an argon atmosphere, there was added 351 mg (1.85 mmol) of tert-butyl-3-amino-2-hydroxypropyl carbamate. The reaction mixture was agitated for 2 hours at room temperature, before being concentrated under reduced pressure. The oil obtained was purified by chromatography on silica gel (AcOEt/heptane: 60/40, v/v). In this way there was obtained 509 mg of the expected intermediate compound (201) in the form of a pale yellow oil (yield: 77%).

$^1$H NMR (CDCl$_3$, 200 MHz):

δ (ppm): 7.84 (d, J=2 Hz, 1H); 7.58-7.30 (m, 1H); 7.40-7.35 (m, 1H); 5.95-5.89 (m, 1H); 5.64-5.50 (m, 3H); 5.17-5.08 (m, 4H); 4.31-4.10 (m, 4H); 3.85-3.79 (m, 1H); 3.36-3.21 (m, 3H); 2.23 (s, 3H); 2.17 (s, 3H); 2.12 (s, 3H); 2.09 (s, 3H); 1.48 (s, 9H); 1.30 (t, J=7 Hz, 2H).

MS (ESI+): 738.2 (M+Na)$^+$, 1453.8 (2M+Na)$^+$.

2) Second Step: Synthesis of the Intermediate (202)

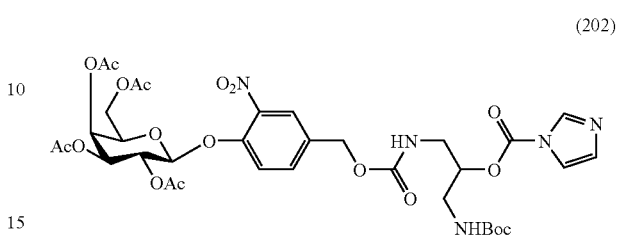

(202)

To a solution of 1.0 g (1.40 mmol) of the intermediate (201) obtained hereinabove in the preceding step in 15 mL of dichloromethane, there were added 45 mg (0.28 mmol) of DMAP and 454 mg (2.80 mmol) of carbonyl diimidazole. The reaction mixture was agitated at room temperature for 12 hours, before being concentrated under reduced pressure. The oil obtained was purified by chromatography on silica gel (AcOEt/heptane: 80/20 v/v). In this way there was obtained 882 mg of the expected intermediate compound (202) in the form of a white foam (yield: 78%).

$^1$H NMR (CDCl$_3$, 200 MHz):

δ (ppm): 8.26 (d, J=7 Hz, 1H); 7.83 (d, J=2 Hz, 1H); 7.57-7.35 (m, 3H); 7.12 (s, 1H); 5.94-5.89 (m, 1H); 5.63-5.45 (m, 3H); 5.18-5.03 (m, 7H); 4.29-4.08 (m, 4H); 3.56-3.51 (m, 4H); 2.23 (s, 3H); 2.17 (s, 3H); 2.11 (s, 3H); 2.08 (s, 3H); 1.47 (s, 9H).

MS (ESI+): 810.1 (M+H)$^+$, 1618.8 (2M+H)$^+$.

3) Third Step: Synthesis of the Intermediate (203)

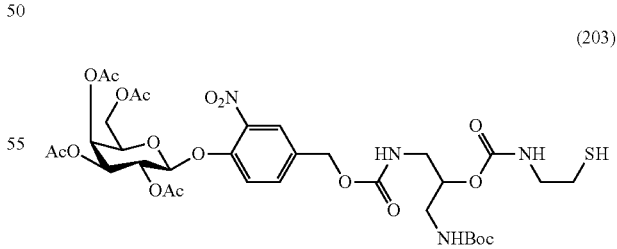

(203)

To a solution of 205 mg (0.253 mmol) of the intermediate (202) obtained hereinabove in the preceding step in 2 mL of anhydrous dichloromethane and under an argon atmosphere, there were added 353 μL (2.50 mmol) of triethylamine and 58 mg (0.506 mmol) of cysteamine hydrochloride. The reaction mixture was agitated at room temperature for 12 hours, before being concentrated under reduced pressure. The oil obtained was purified by chromatography on silica gel (AcOEt/heptane: 60/40 v/v). In this way there was obtained 130 mg of the expected intermediate compound (203) in the form of a pale yellow oil (yield: 63%).

$^1$H NMR (CDCl$_3$, 200 MHz):

δ(ppm): 7.84 (d, J=2 Hz, 1H); 7.56 (dd, J=2 and 9 Hz, 1H); 7.37 (d, J=9 Hz, 1H); 5.73-5.66 (m, 1H); 5.63-5.48 (m, 2H); 5.19-5.08 (m, 4H); 4.99-4.91 (m, 1H); 4.80-4.72 (m, 1H); 4.34-4.07 (m, 3H); 3.54-3.24 (m, 4H); 2.92 (d, J=7 Hz, 4H); 2.23 (s, 3H); 2.17 (s, 3H); 2.12 (s, 3H); 2.06 (s, 3H); 1.48 (s, 9H).

MS (ESI+): 841.2 (M+Na)$^+$; 1659.8 (2M+Na)$^+$.

4) Fourth Step: Synthesis of the Intermediate (204)

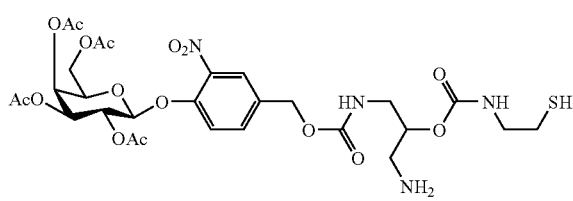

(204)

To a solution, cooled to 0° C. under an argon atmosphere, of 210 mg (0.256 mmol) of the intermediate (203) obtained hereinabove in the preceding step in 3 mL of anhydrous dichloromethane, there was added 1 mL (13.0 mmol) of trifluoroacetic acid. The reaction mixture was agitated for 2 hours at 0° C., before being hydrolyzed with an aqueous sodium hydrogen carbonate solution. The aqueous phase was extracted two times with 50 mL of dichloromethane; the organic phase obtained was washed two times with 50 mL of water, dried over magnesium sulfate, filtered over sintered glass then concentrated under reduced pressure. In this way there was obtained 117 mg of the expected intermediate compound (204) in the form of a pale yellow oil (yield: 64%). The product was then used directly in the following step, without additional purification.

$^1$H NMR (CDCl$_3$, 200 MHz):

δ (ppm): 7.83 (d, J=2 Hz, 1H); 7.57 (dd, J=2 and 9 Hz, 1H); 7.39 (d, J=9 Hz, 1H); 5.63-5.50 (m, 2H); 5.34 (s, 3H, 5.19-5.08 (m, 4H); 4.82-4.76 (m, 1H); 4.31-4.11 (m, 3H); 3.54-3.35 (m, 3H); 2.97-2.91 (m, 3H); 2.22 (s, 3H); 2.16 (s, 3H); 2.11 (s, 3H); 2.05 (s, 3H); 1.38-1.19 (m, 2H); 1.02-0.91 (m, 1H).

MS (ESI+): 741.3 (M+Na)$^+$; 1459.2 (2M+Na)$^+$.

5) Fifth Step: Synthesis of the Intermediate (205)

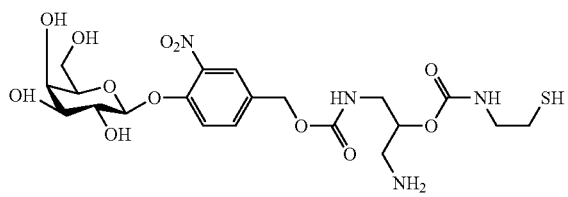

(205)

To a solution of 117 mg (0.163 mmol) of the intermediate (204) obtained hereinabove in the preceding step in 2 mL of anhydrous methanol and under an argon atmosphere, there was added 9 mg (0.163 mmol) of sodium methylate. The reaction mixture was agitated at room temperature for 12 hours. The pH of the solution was then adjusted to pH=7 by adding H$^+$/Na$^+$ ion-exchange resin. In this way there was obtained 45 mg of the expected intermediate compound (205) in the form of a pale yellow solid (yield: 50%). The product was then used directly in the following step, without additional purification.

$^1$H NMR (CDCl$_3$, 200 MHz):

δ (ppm): 7.84-7.22 (m, 3H); 5.09-4.87 (m, 4H); 3.89 (d, J=3 Hz, 1H); 3.79-3.61 (m, 6H); 3.30-3.05 (m, 4H); 2.67-2.62 (m, 4H).

MS (ESI+): 519.3 (M-S)$^+$; 541.2 (M-S+Na)$^+$; 550.5 (M+H)$^+$; 573.3 (M+Na)$^+$; 1099.4 (2M-2H)$^+$.

6) Sixth Step: Synthesis of the Intermediate (206)

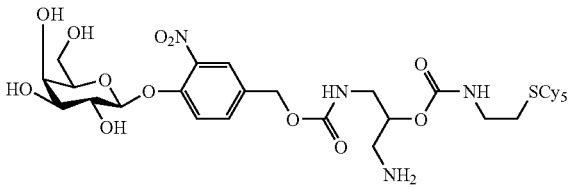

(206)

To a solution of 0.674 mg (1.22 µmol) of the intermediate (205) obtained hereinabove in the preceding step in 150 µL of 0.01 mol/L PBS buffer solution (pH=7.4), there was added 48 µL (24 µmol) of a 0.5 mol/L solution of tris(2-carboxyethyl) phosphine hydrochloride. The reaction mixture was agitated for 30 minutes at room temperature, before the addition of a solution of 1.0 mg (1.22 µmol) of Cy5 monomaleimide in 50 µL of DMSO. The reaction mixture was agitated for 12 hours at room temperature and shielded from light, before being directly purified by HPLC to produce 0.77 mg of the expected intermediate compound (206) (yield: 46%).

MS (ESI-): 1327.4 (M-H)$^-$.

7) Sixth Step: Synthesis of the Compound (200) According to the Invention

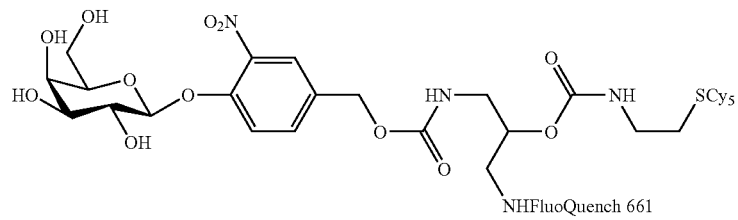

(200)

To a solution of 0.77 mg (0.561 μmol) of the intermediate (206) obtained hereinabove in the preceding step in 50 μL of N,N-dimethylformamide, there were added 5 μL (36 μmol) of triethylamine and a solution of 1.0 mg (1.12 μmol) of Fluo-Quench 661 mono NHS ester in 50 μL of N,N-dimethylformamide. The reaction mixture was agitated for 12 hours at room temperature and shielded from light, before being directly purified by HPLC to produce 0.52 mg of the compound (200) according to the invention (yield: 45%).

MS (ESI-): 2056.6 (M-H)$^-$.

The invention claimed is:

1. An enzymatic substrate of structure (I):

[Sac]-B(I)F wherein:
[Sac] is at least one saccharidic unit selected from the group consisting of monosaccharides, an oligosaccharide having 2 to 9 saccharidic units and polysaccharides having at least 10 saccharidic units;
B is a self-cleavable spacer arm comprising at least two subunits, selected from B spacer arms according to i) or ii), wherein
B spacer arm i) comprises:
a monocyclic aromatic group of formula (II) and an aromatic group of formula (III);

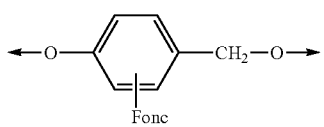

(II)

wherein
Fonc is a chemical function that is reactive toward a complementary chemical function of a fluorophore group F or a group I that inhibits the fluorescence of the fluorophore group F,
the arrow starting at the oxygen atom carried directly by the phenyl ring represents the point of attachment to a saccharidic unit of the spacer arm via a covalent bond with the carbon atom situated in anomeric position 1 of the saccharidic unit,
the arrow starting at the oxygen atom connected to the —CH$_2$— radical represents the point of attachment to the aromatic group of formula (III):

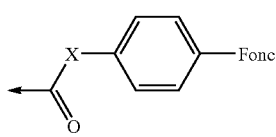

(III)

wherein
Fonc is a chemical function that is reactive toward a complementary chemical function of a group I that inhibits the fluorescence of the group F or toward a complementary chemical function of a fluorophore group F,
the arrow represents the point of attachment to the oxygen atom of the monocyclic aromatic group of formula (II),
X is O, NH or S; and
B spacer arm ii) comprises: a monocyclic aromatic group of formula (IV), a group of formula (V) and a group of formula (VI):

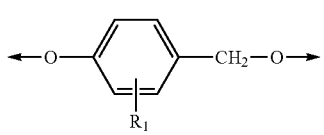

(IV)

wherein:
R$_1$ is selected from the group consisting of nitro, sulfate, amine groups and an amine protected by a protective group,
the arrow starting at the oxygen atom carried directly by the carbon atom of the phenyl ring represents the point of attachment to a saccharidic unit of the spacer arm via a covalent bond with the carbon atom in anomeric position 1 of the saccharidic unit,
the arrow starting at the oxygen atom attached to the —CH$_2$— radical represents the point of attachment of to a group of the formula (V):

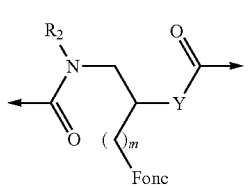

(V)

wherein:
R$_2$ is a hydrogen atom or a C$_1$-C$_4$ alkyl radical,
Fonc is a chemical function that is reactive toward a complementary chemical function of a fluorophore group F or toward a complementary chemical function of a group I that inhibits the fluorescence of a fluorophore group F,
m is an integral number ranging from 1 to 10,
Y is O, NH or S,
the arrows represent the point of attachment to the group of formula (III) on the one hand and to the group of formula (VI) on the other hand:

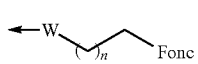

(VI)

wherein:
W represents O, NH or S,
the arrow represents the point of attachment of the nitrogen, sulfur or oxygen atom denoted by W via a covalent bond with a carbon atom of the group of formula (V),
n is an integral number ranging from 1 to 10,
Fonc is a chemical function that is reactive toward a complementary chemical function of a fluorophore group F or toward a complementary chemical function of a group I that inhibits the fluorescence of a fluorophore group F,
F is a fluorophore group carried by the spacer arm;
I is a group that inhibits the fluorescence of F when in structure (I) and is a side substituent of the spacer arm; and
with the proviso that the fluorophore group F is not connected directly to the inhibitor group I by any covalent bond.

2. The substrate according to claim 1, wherein [Sac] is selected from the group consisting of galactose, mannose, idose, talose, rhamnose, glucose, ribose, fucose and amino or acid derivatives thereof.

3. The substrate according to claim 2 wherein [Sac] is selected from the group consisting of galactosamine, glucosamine, lactosamine, glucuronic acid, iduronic acid and sialic acid.

4. The substrate according to claim 2, wherein [Sac] is selected from the group consisting of glucosamine, galactose and glucuronic acid.

5. The substrate according to claim 1, wherein [Sac] is an oligosaccharide having 4 to 9 saccharidic units.

6. The substrate according to claim 1 wherein Fonc is a primary amine or a thiol.

7. The substrate according to claim 1, wherein the self-cleavable spacer arm is B spacer arm i) and in formula (II) Fonc is ortho to the carbon atom carrying the oxygen atom.

8. The substrate according to claim 1, wherein the self-cleavable spacer arm is B spacer arm i) and in formula (III)-X is an oxygen atom and Fonc is a primary amine or thiol function, or
X is a nitrogen atom and Fonc is a primary amine or thiol function.

9. The substrate according to claim 1, wherein the self-cleavable spacer arm is B spacer arm ii) and in formula (IV) $R_1$ is ortho to the carbon atom carrying the oxygen atom.

10. The substrate according to claim 1, wherein the self-cleavable spacer arm is B spacer arm ii) and in formula (V)
$R_2$ is a methyl radical, m=1, Fonc is a primary amine function and Y is an oxygen atom, or
$R_2$ is a methyl radical, m=1, Fonc is a primary amine function and Y=NH.

11. The substrate according to claim 1, wherein the self-cleavable spacer arm is B spacer arm ii) and in formula (VI)
W is an oxygen atom, n=1, Fonc is a primary amine function and Y is an oxygen atom, or
W represents NH, n=1, Fonc is a primary amine function and Y is an oxygen atom, or
W is a sulfur atom, n=1, Fonc is a primary amine function and Y is an oxygen atom.

12. The substrate according to claim 1, wherein the substrate of formula I is a compound of formula (I-1) or (I-2):

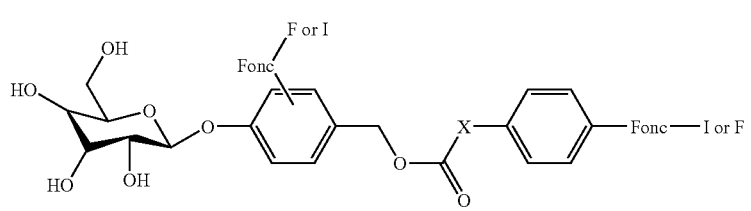

(I-1)

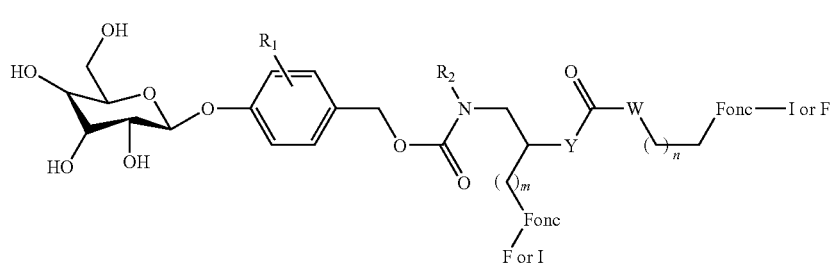

(I-2)

wherein F, I, Fonc, X, Y, W, $R_1$, $R_2$, m and n are as described in claim 1.

13. The substrate according to claim 1, wherein the fluorophore groups F are selected from the group consisting of fluorescein and its derivatives; fluorescent dyes that absorb and emit in the near infrared; fluorescent cyanines; 7-hydroxy-9H-(1,3-dichloro-9,9-dimethylacridin-2-one); rhodamine and its derivatives; fluorescent dyes containing reactive amines; dipyrromethene boron difluorides; porphyrins; cyanines; oxazines; fluorophores derived from pyrene; diazo derivatives of pyrene; dansyl derivatives of pyrene; eosin; erythrosine; derivatives of sulforhodamine; and fluorescent nanoparticles.

14. The substrate according to claim 13, wherein F absorbs and emits in the near infrared.

16. The substrate according to claim 15, wherein I is identical to F.

15. The substrate according to claim 1, wherein I is a fluorescent group and the fluorescence of I inhibits the fluorescence of group F.

17. The substrate according to claim 1, wherein I is a fluorescent group that is different from the group F and that I absorbs the fluorescence of the group F by fluorescence resonance energy transfer.

18. The substrate according to claim 1, wherein the substrate is selected from the group of compounds of formula (I) wherein:
i) [Sac] is a galactosamine, the spacer arm comprises subunit of formula (II) and a subunit of formula (III), and F and I are identical;
ii) [Sac] is a galactosamine, the spacer arm comprises a subunit of formula (IV), a subunit of formula (V) and a subunit of formula (VI), and F and I are identical; and
iii) [Sac] is a galactosamine, the spacer arm comprises a subunit of formula (IV) and a subunit of formula (III), and F and I are different.

19. The substrate according to claim 12, wherein the enzymatic substrate of formula (I-1) is one of formula (7) or (105):

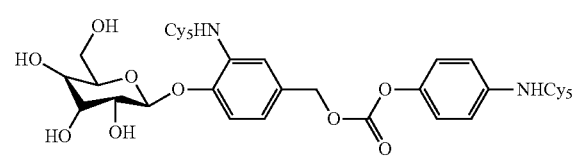

(7)

-continued

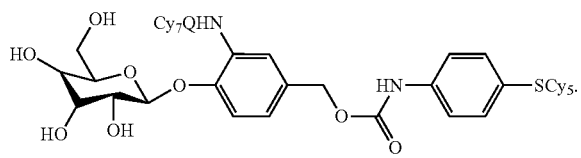

(105)

20. The substrate according to claim 12, wherein the enzymatic substrate is of formula (I-2) and has a structure of formula (13):

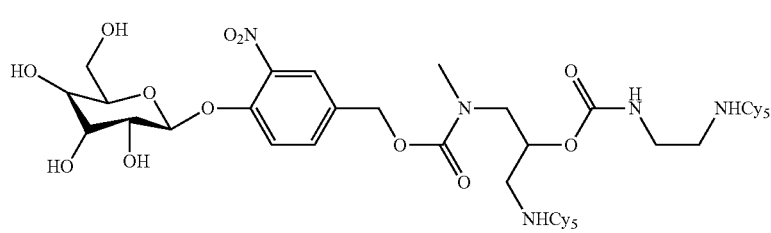

(13)

21. A process of detection of enzymatic activity in vitro, comprising:
   a) contacting an enzyme with at least one substrate of formula (I) according to claim 1; and
   b) detecting the fluorescence of the fluorophore group F.

22. A process of manufacture of a diagnostic reagent for functional imaging in vivo, comprising formulating the diagnostic reagent to comprise at least one substrate of formula (I) according to claim 1 wherein F absorbs and emits in the near infrared.

23. A process for imaging, by fluorescence, the expression of the reporter genes lacZ and gusA of *E. coli.* comprising detecting fluorescence due to enzymatic cleavage of at least one substrate of formula (I) according to claim 1 wherein F absorbs and emits in the near infrared.

24. A diagnostic reagent, comprising:
   water or of a mixture of water and at least one organic solvent, and
   at least one enzymatic substrate of formula (I) as defined in claim 1.

25. The reagent according to claim 24, wherein the reagent is an in vivo diagnostic reagent and the enzymatic substrate of formula (I) comprises at least one fluorophore group F that absorbs and emits in the near infrared.

26. The reagent according to claim 24 wherein a concentration of the enzymatic substrate or substrates of formula (I) is from 1 μM to 1 mM.

27. The reagent according to claim 25 wherein a concentration of the enzymatic substrate or substrates of formula (I) is from 1 μM to 1 mM.

* * * * *